United States Patent
Ishidai et al.

(10) Patent No.: US 10,483,471 B2
(45) Date of Patent: Nov. 19, 2019

(54) ORGANIC ELECTROLUMINESCENT ELEMENT, METHOD FOR PRODUCING ORGANIC ELECTROLUMINESCENT ELEMENT, DISPLAY, AND LIGHTING DEVICE

(71) Applicant: KONICA MINOLTA, INC., Chiyoda-ku (JP)

(72) Inventors: Keiko Ishidai, Hachioji (JP); Shinya Otsu, Koganei (JP); Noboru Sekine, Hino (JP)

(73) Assignee: Konica Minolta, Inc., Tokyo (JP)

(*) Notice: Subject to any disclaimer, the term of this patent is extended or adjusted under 35 U.S.C. 154(b) by 133 days.

(21) Appl. No.: 15/400,279

(22) Filed: Jan. 6, 2017

(65) Prior Publication Data

US 2017/0194574 A1    Jul. 6, 2017

(30) Foreign Application Priority Data

Jan. 6, 2016 (JP) .................. 2016-001236

(51) Int. Cl.
*H01L 51/50* (2006.01)
*H01L 51/00* (2006.01)
(Continued)

(52) U.S. Cl.
CPC ........ *H01L 51/0073* (2013.01); *C07D 403/14* (2013.01); *C07D 405/14* (2013.01);
(Continued)

(58) Field of Classification Search
None
See application file for complete search history.

(56) References Cited

U.S. PATENT DOCUMENTS

2013/0056720 A1* 3/2013 Kim ............... C07D 401/14
                                                             257/40
2015/0336937 A1* 11/2015 Lee ............... C07D 405/14
                                                             257/40
(Continued)

FOREIGN PATENT DOCUMENTS

CN        102971395        3/2013
CN        104039778        9/2014
(Continued)

OTHER PUBLICATIONS

Office Action dated Apr. 5, 2018 which issued in the corresponding Korean Patent Application No. 10-2016-0177310.
(Continued)

*Primary Examiner* — Gregory D Clark
(74) *Attorney, Agent, or Firm* — Cozen O'Connor

(57) ABSTRACT

Provided are an organic electroluminescent (EL) element having high luminescent efficiency, a small aging change in luminescent intensity even after the organic EL element is stored at a high temperature together with a long luminescent lifetime at a high temperature, and a method for producing the organic EL element. Further, a display and a lighting device including the organic EL element are also provided. The organic EL element contains an organic layer provided between at least a pair of a cathode and an anode. The organic layer is formed of at least one layer including a luminescent layer, and at least one layer forming the organic layer contains at least one of the compounds represented by the general formulae (A1) to (A5).

(Continued)

(A-1)

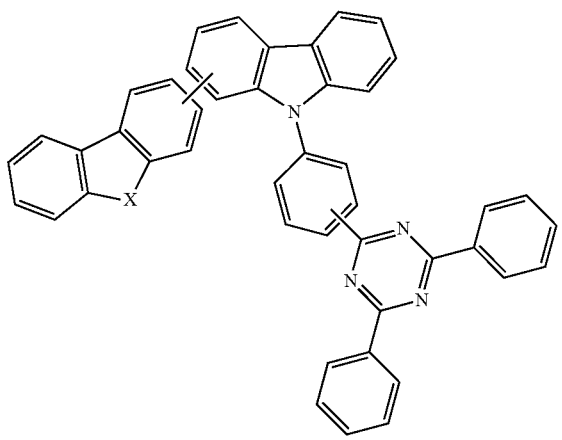

(A-2)

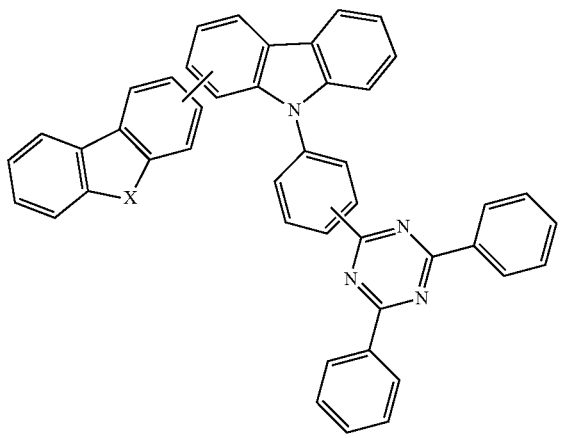

(A-3)

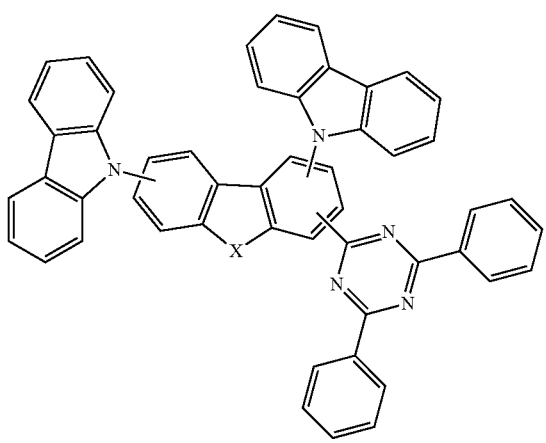

-continued (A-4)

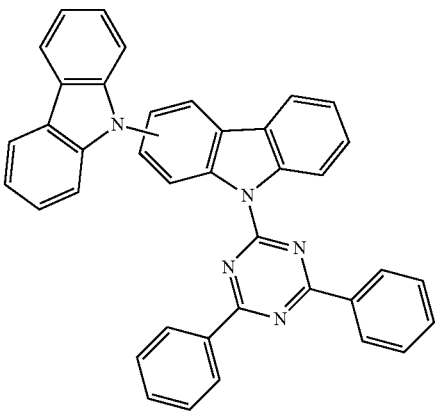

(A5)

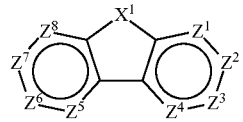

7 Claims, 2 Drawing Sheets

(51) Int. Cl.
| | |
|---|---|
| *C07D 405/14* | (2006.01) |
| *C09K 11/06* | (2006.01) |
| *C07D 403/14* | (2006.01) |
| *C07D 519/00* | (2006.01) |
| *C07D 491/048* | (2006.01) |
| *C09K 11/02* | (2006.01) |

(52) U.S. Cl.
CPC ....... *C07D 491/048* (2013.01); *C07D 519/00* (2013.01); *C09K 11/025* (2013.01); *C09K 11/06* (2013.01); *H01L 51/0067* (2013.01); *H01L 51/0071* (2013.01); *H01L 51/0072* (2013.01); *H01L 51/0085* (2013.01); *C09K 2211/1007* (2013.01); *C09K 2211/1029* (2013.01); *C09K 2211/185* (2013.01); *H01L 51/5016* (2013.01); *H01L 51/5072* (2013.01)

(56) References Cited

U.S. PATENT DOCUMENTS

| | | | |
|---|---|---|---|
| 2015/0349268 A1* | 12/2015 | Zeng | H01L 51/0067 257/40 |
| 2016/0233436 A1* | 8/2016 | Zeng | H01L 51/0072 |
| 2017/0133599 A1* | 5/2017 | Cho | H01L 51/0072 |

FOREIGN PATENT DOCUMENTS

| | | |
|---|---|---|
| CN | 104662023 | 5/2015 |
| EP | 2568030 | 3/2013 |
| JP | 2011-084531 | 4/2011 |
| JP | 5831654 | 12/2015 |
| KR | 20110015836 | 2/2011 |
| KR | 20140099082 | 8/2014 |
| KR | 20150010387 | 1/2015 |
| KR | 10-2015-0100555 | 9/2015 |
| KR | 10-2015-0133998 | 12/2015 |
| KR | 10-2015-0136942 | 12/2015 |
| WO | WO 2010/083359 | 7/2010 |
| WO | WO 2010/136109 | 12/2010 |

(56) References Cited

FOREIGN PATENT DOCUMENTS

| WO | WO 2011/019156 | 2/2011 |
| WO | WO 2013/012298 | 1/2013 |
| WO | WO 2014/044722 | 3/2014 |
| WO | WO 2015/022987 | 2/2015 |

OTHER PUBLICATIONS

Office Action dated Mar. 28, 2018 which issued in the corresponding Chinese Patent Application No. 201710008648.7.
Search Report dated Jun. 29, 2017 which issued in the corresponding European Patent Application No. 17150236.2.
Search Report dated Nov. 17, 2017 which issued in the corresponding European Patent Application No. 17150236.2.
Office Action dated Nov. 26, 2018 issued in Korean Patent Application No. 10-2016-0177310.
Office Action dated Dec. 5, 2018 issued in Chinese Patent Application No. 201710008648.7.

* cited by examiner

LIGHT

LIGHT

ORGANIC ELECTROLUMINESCENT ELEMENT, METHOD FOR PRODUCING ORGANIC ELECTROLUMINESCENT ELEMENT, DISPLAY, AND LIGHTING DEVICE

BACKGROUND OF THE INVENTION

1. Field of the Invention

The present invention relates to an organic electroluminescent element, a method for producing an organic electroluminescent element, a display, and a lighting device.

2. Description of Related Art

An organic electroluminescent element (hereinafter, referring to as an "organic EL element") is a thin film type of all-solid element formed of layers of an organic thin film (e.g., a single layer member or a multi layer member) containing an organic luminescent substance provided between a cathode and an anode. When a voltage is applied to such an organic EL element, electrons are injected from a cathode into an organic thin film layer, and holes are injected from an anode into the layer. Then, holes and electrons are recombined in a luminescent layer (i.e., an organic luminescent substance-containing layer) thereby generating excitons.

An organic EL element is a luminescent element using light emission (i.e., fluorescence and phosphorescence) of the excitons. Therefore, technologically, an organic EL element is expected to be applied to a next-generation flat display and lighting apparatus.

Further, researchers of the Princeton University reported an organic EL element using phosphorescent luminescence out of a triplet excitation state, with realizing about 4-times higher luminescent efficiency in principle than an organic EL element using fluorescent luminescence. After the report was published, development has started focusing on materials emitting phosphorescence at a room temperature, and the research and development have been extensively carried out focusing on layer structures of light emitting elements and electrodes.

As described above, a phosphorescent luminescence system has a high potentiality. However, greatly different from an organic EL device using fluorescent luminescence, an organic EL device using phosphorescent luminescence has important technological issues how to control a center position of luminescence, especially how to recombine holes and electrons inside a luminescent layer, and how to stably emit light, in order to improve the luminescent efficiency and lifetime of the device.

Hereby, mixed layers including a phosphorescent luminescence compound acting as a luminescent dopant, and a host compound are generally used in luminescent layers.

Meanwhile, in view of materials, there are high expectations for creating novel materials having improved performance of element. For example, WO2011/019156 and WO2010/083359 disclose specific triazine compounds and specific condensed ring aromatic heterocyclic compounds both of which are used for a host compound of a phosphorescent luminescence compound.

When an organic EL element used those specific compounds disclosed in WO2011/019156 and WO2010/083359 as a host compound, the luminescent efficiency of the element was mostly improved. However, remarkable decrease in luminescent intensity was observed, after the organic EL element deposited with those compounds was stored at a high temperature. Further, it was revealed that the luminescent lifetime of the element when stored at a high temperature became shorter than the element when stored at a room temperature. Moreover, there is room for further improving the luminescent efficiency.

SUMMARY OF THE INVENTION

The present invention has been made in view of the above defects and circumstance. An object of the present invention is to provide an organic electroluminescent element including specific aromatic heterocyclic derivatives, the organic EL element having high luminescent efficiency, a small aging variation of luminescent intensity after storage at a high temperature, and a long luminescent lifetime at a high temperature, and a method for producing the organic EL element. Further, another object is to provide a display and a lighting device including the organic EL element.

The present inventors have earnestly investigated causes of the defects, and eventually found out that aromatic heterocyclic derivatives having specific structures effectively solve those defects.

Namely, the defects targeted by the inventors may be solved by the following aspects.

(Aspect 1)

An organic electroluminescent element containing at least an organic layer provided between a pair of electrodes (i.e., a cathode and an anode, in which the organic layer is formed of at least one layer including a luminescent layer, and at least one of the organic layer contains at least one selected from compounds represented by the following general formulae (A1) to (A5).

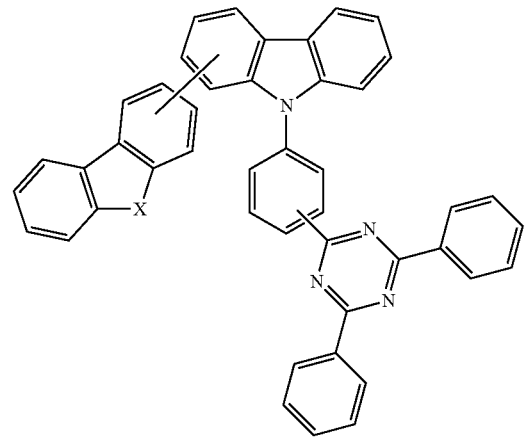

General Formula (A1)

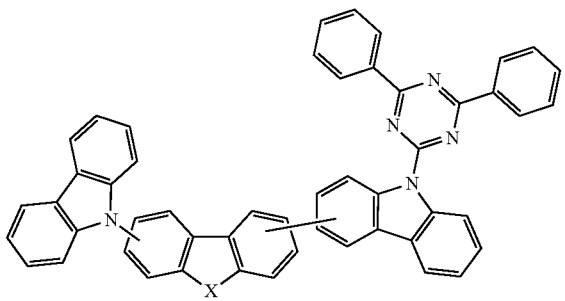

General Formula (A2)

General Formula (A3)

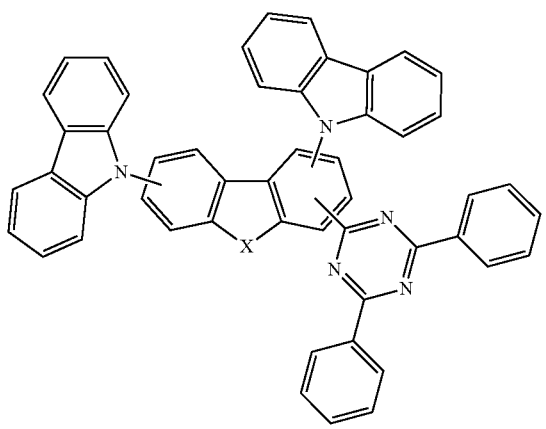

[in general formulae (A1) to (A3), X represents an oxygen atom or a sulfur atom.]

General Formula (A4)

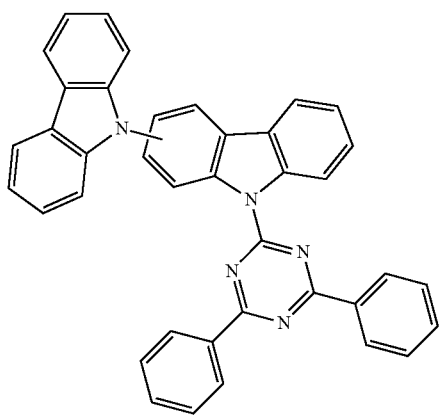

General Formula (A5)

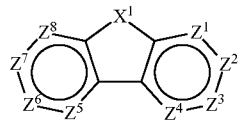

[in the general formulae (A5), $X^1$ represents an oxygen atom or a sulfur atom; $Z^1$ to $Z^8$ independently represent =N— or =C($R^1$)—; $R^1$ represents a hydrogen atom or a substituent, at least one of $Z^1$ to $Z^4$ represents =N—. Note, when $Z^4$ is =N—, $Z^1$ represents =N— or =C($R^2$)—, and $R^2$ represents a nitrogen-containing 6 membered heterocycle of the following general formula (A5-1). Further, when $Z^4$ is =C($R^1$)—, at least $Z^3$ represents =N—.]

General Formula (A5-1)

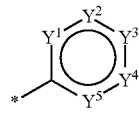

[in the general formula (A5-1), $Y^1$ to $Y^5$ independently represent =N— or =C($R^3$)—; $R^3$ represents a hydrogen atom or a substituent; at least one of $Y^1$-$Y^5$ represents =N—; * represents a linkage position to the general formula (A5). Note, when two of =C($R^3$)— are adjacently placed in series, two of $R^3$ may be condensed together to form a ring.]

General Formula (A5-2)

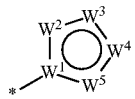

[in the general formula (A5-2), $W^1$ represents —N— or =C—; $W^2$ to $W^5$ independently represent =N— or =C($R^4$)—; $R^4$ represents a hydrogen atom or a substituent; at least one of $W^1$ to $W^5$ represents =N—; * represents a linkage position to the general formula (A5). Note, when two of =C($R^4$)— are adjacently placed in series, two of $R^4$ may be condensed together to form a ring.

(Aspect 2)

An organic electroluminescent element including an organic layer that is disposed between at least a pair of a cathode and an anode. Herein, the organic layer is formed of at least one layer including a luminescent layer, and at least one layer forming the organic layer contains at least one compound selected from the compounds represented by the general formulae (A1) to (A5).

General Formula (A1)

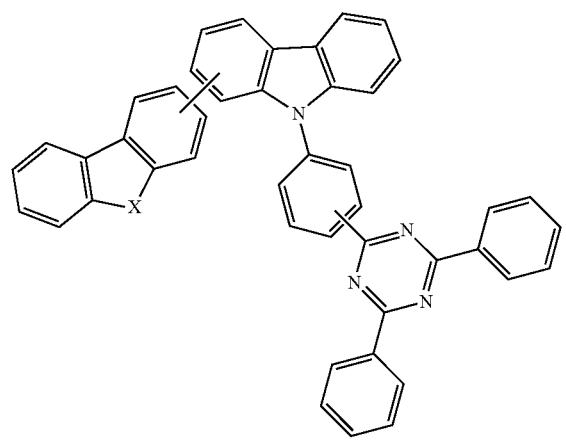

General Formula (A2)

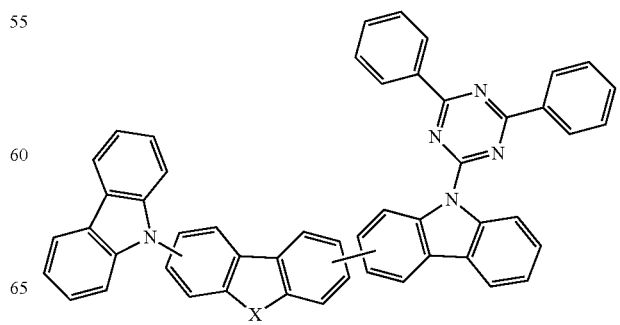

General Formula (A3)

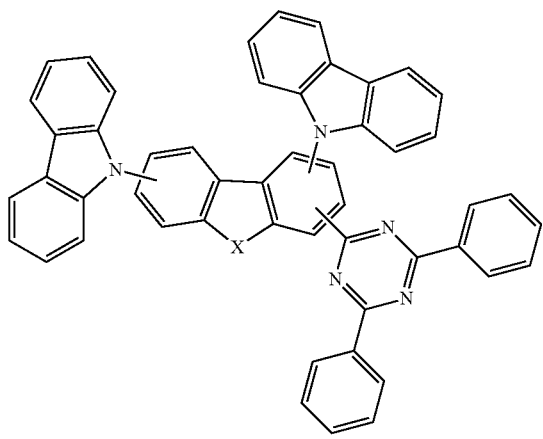

[in the general formulae (A1) to (A3), X represents an oxygen atom or a sulfur atom.]

General Formula (A4)

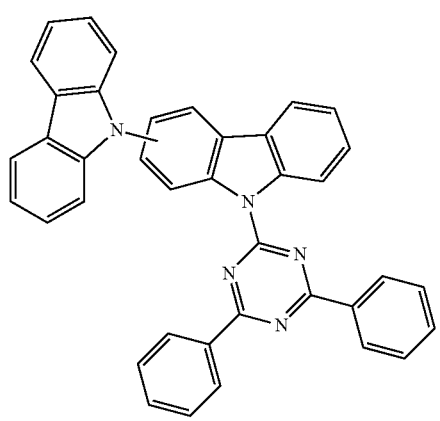

General Formula (A5)

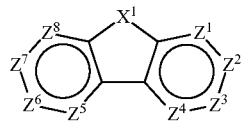

[in the general formula (A5), $X^1$ represents an oxygen atom or a sulfur atom, $Z^1$ to $Z^8$ independently represent =N— or =C($R^1$)—, $R^1$ represents a hydrogen atom or a substituent, at least one of $Z^1$ to $Z^4$ represents =N—, remaining ones of $Z^1$ to $Z^4$ represent =C($R^1$)—. Note, when $Z^4$ is =N—, $Z^1$ represents =N— or =C($R^2$)—, at least one of $R^1$ in the remaining ones of $Z^1$ to $Z^4$ represents a nitrogen-containing 6 membered heterocycle of the following general formula (A5-1).]

General Formula (A5-1)

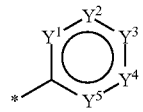

[in the general formula (A5-1), $Y^1$ to $Y^5$ independently represent =N— or =C($R^3$)—, $R^3$ represents a hydrogen atom or a substituent, at least one of $Y^1$ to $Y^5$ represents =N—, * represents a linkage position to the general formula (A5). Note, when two of =C($R^3$)— are adjacently placed in series, two of $R^3$ may be condensed together to form a ring.]

(Aspect 3)

An organic electroluminescent element including an organic layer that is disposed between at least a pair of a cathode and an anode. Herein, the organic layer is formed of at least one layer including a luminescent layer, and at least one layer forming the organic layer contains at least one compound selected from the compounds represented by the general formulae (A1) to (A5).

General Formula (A1)

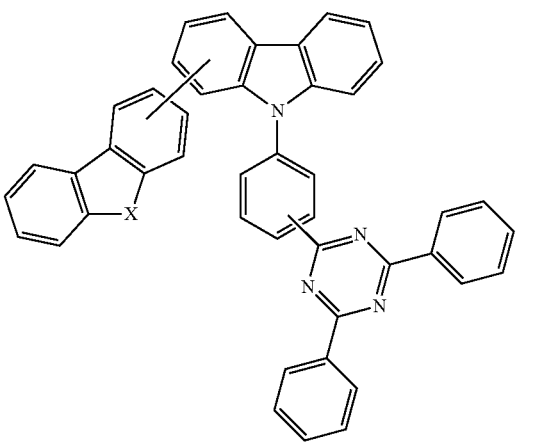

General Formula (A2)

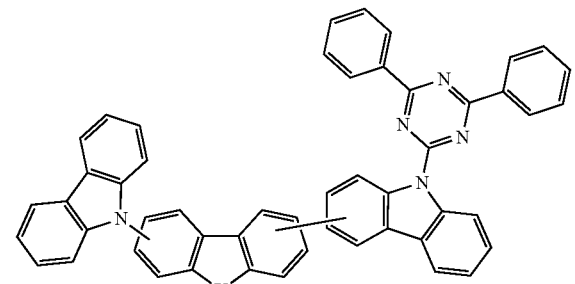

General Formula (A3)

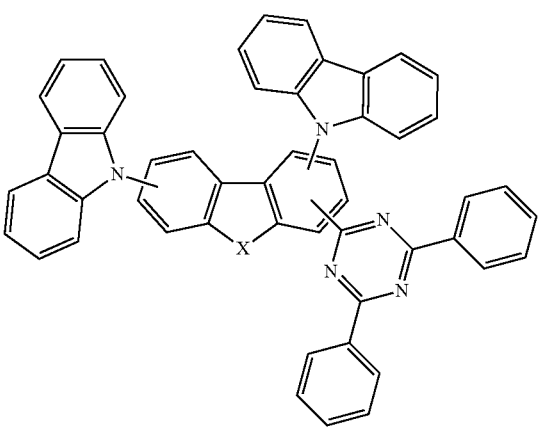

[in the general formulae (A1) to (A3), X represents an oxygen atom or a sulfur atom.]

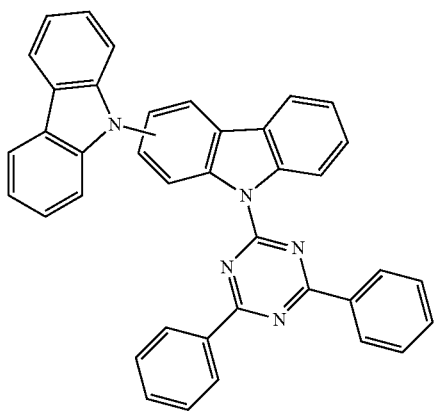

General Formula (A4)

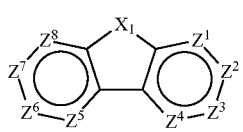

General Formula (A5)

[in the general formula (A5), $X^1$ represents an oxygen atom or a sulfur atom, $Z^1$ to $Z^3$ represent =C($R^1$)—, $Z^4$ represents =N—, $Z^5$ to $Z^8$ independently represent =N— or =C($R^1$)—, $R^1$ represents a hydrogen atom or a substituent, at least one of $R^1$ in $Z^1$ to $Z^3$ represents a nitrogen-containing 6 membered heterocycle of the following general formula (A5-1).]

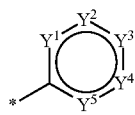

General Formula (A5-1)

[in the general formula (A5-1), $Y^1$ to $Y^5$ independently represent =N— or =C($R^3$)—; $R^3$ represents a hydrogen atom or a substituent; at least one of $Y^1$ to $Y^5$ represents =N—; * represents a linkage position to the general formula (A5). Note, when two of =C($R^3$)— are adjacently placed in series, two of $R^3$ may be condensed together to form a ring.]

(Aspect 4)

An organic electroluminescent element described in the aspect 1. Herein, at least one layer forming the organic layer contains compounds represented by the following general formula (A5).

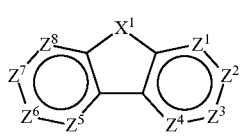

General Formula (A5)

[in the general formula (A5), $X^1$ represents an oxygen atom or a sulfur atom, $Z^1$ to $Z^8$ independently represent =N— or =C($R^1$)—, $R^1$ represents a hydrogen atom or a substituent, at least one of $Z^1$ to $Z^4$ represents =N—, remaining ones of $Z^1$ to $Z^4$ represent =C($R^1$)—, at least one of $R^1$ in the remaining ones of $Z^1$ to $Z^4$ represents a nitrogen-containing 6 membered heterocycle of the following general formula (A5-1).]

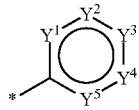

General Formula (A5-1)

[in the general formula (A5-1), $Y^1$ to $Y^5$ independently represent =N— or =C($R^3$)—, $R^3$ represents a hydrogen atom or a substituent, at least one of $Y^1$ to $Y^5$ represents =N—, * represents a linkage position to the general formula (A5). Note, when two of =C($R^3$)— are adjacently placed in series, two of $R^3$ may be condensed together to form a ring.]

(Aspect 5)

An organic electroluminescent element described in the aspect 1 or 2. Herein, at least one layer forming the organic layer contains compounds represented by the following general formula (A5).

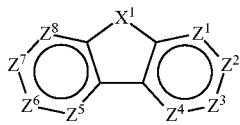

General Formula (A5)

[in the general formulae (A5), $X^1$ represents an oxygen atom or a sulfur atom, $Z^1$ to $Z^3$ represent =C($R^1$)—, $Z^4$ represents =N—, $Z^5$ to $Z^8$ independently represent =N— or =C($R^1$)—, $R^1$ represents a hydrogen atom or a substituent, at least one of $R^1$ in $Z^1$ to $Z^3$ represents a nitrogen-containing 6 membered heterocycle of the following general formula (A5-1).]

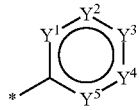

General Formula (A5-1)

[in the general formula (A5-1), $Y^1$ to $Y^5$ independently represent =N— or =C($R^3$)—, $R^3$ represents a hydrogen atom or a substituent, at least one of $Y^1$ to $Y^5$ represents =N—, * represents a linkage position to the general formula (A5). Note, when two of =C($R^3$)— are adjacently placed in series, two of $R^3$ may be condensed together to form a ring.]

(Aspect 6)

An organic electroluminescent element described in any one of the aspects 1 to 5. Herein, the general formula (A5-1) is represented by the following general formula (A5-3) or (A5-4).

General Formula (A5-3)

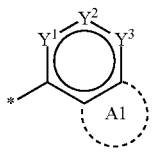

[in the general formula (A5-3), $Y^1$ to $Y^3$ independently represent =N— or =C($R^3$)— respectively; $R^3$ represents a hydrogen atom or a substituent; at least one of $Y^1$ to $Y^3$ represents =N—; * represents a linkage position to the general formula (A5). A1 represents a residue forming a 6 membered aryl, 6 membered heteroaryl or 5 membered heteroaryl ring.]

General Formula (A5-4)

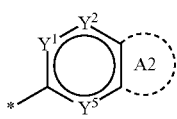

[in the general formula (A5-4), $Y^1$, $Y^2$ and $Y^5$ independently represent =N— or =C($R^3$)— respectively; $R^3$ represents a hydrogen atom or a substituent; at least one of $Y^1$, $Y^2$ and $Y^5$ represents =N—; * represents a linkage position to the general formula (A5). A2 represents a residue forming a 6 membered aryl, 6 membered heteroaryl or 5 membered heteroaryl ring.]

(Aspect 7)
An organic electroluminescent element described in the aspect 6. Herein, the general formula (A5-1) is represented by the general formula (A5-4) and the general formula (A5-4) is represented by the following general formula (A5-5) or (A5-6).

General Formula (A5-5)

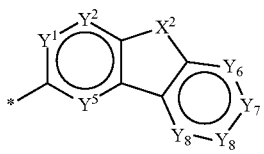

[in the general formula (A5-5), $Y^1$, $Y^2$, and $Y^5$ to $Y^9$ independently represent =N— or =C($R^3$)— respectively; $R^3$ represents a hydrogen atom or a substituent; at least one of $Y^1$, $Y^2$ and $Y^5$ represents =N—; * represents a linkage position to the general formula (A5). $X^2$ represents one member selected from an oxygen atom, a sulfur atom, $NR^2$ or $CR^3R^4$. $R^2$ and $R^4$ are identical to the above described $R^2$ and $R^4$, respectively.]

General Formula (A5-6)

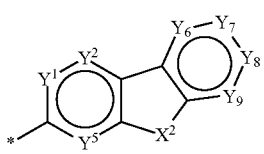

[in the general formula (A5-6), $Y^1$, $Y^2$, and $Y^5$ to $Y^9$ independently represent =N— or =C($R^3$)— respectively; $R^3$ represents a hydrogen atom or a substituent; at least one of $Y^1$, $Y^2$ and $Y^5$ represents =N—; * represents a linkage position to the general formula (A5). $X^2$ represents one member selected from an oxygen atom, a sulfur atom, $NR^2$ or $CR^3R^4$. $R^2$ and $R^4$ are identical to the above described $R^2$ and $R^4$, respectively.]

(Aspect 8)
An organic electroluminescent element described in the aspect 6. Herein, the general formula (A5-1) is represented by the general formula (A5-3) and the general formula (A5-3) is represented by the following general formula (A5-7) or (A5-8).

General Formula (A5-7)

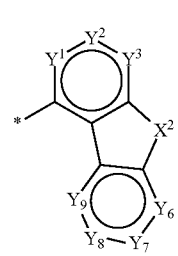

[in the general formula (A5-7), $Y^1$ to $Y^3$, and $Y^6$ to $Y^9$ independently represent =N— or =C($R^3$)— respectively; $R^3$ represents a hydrogen atom or a substituent; at least one of $Y^1$ to $Y^3$ represents =N—; * represents a linkage position to the general formula (A5). $X^2$ represents one member selected from an oxygen atom, a sulfur atom, $NR^2$ or $CR^3R^4$. $R^2$ and $R^4$ are identical to the above described $R^2$ and $R^4$, respectively.]

General Formula (A5-8)

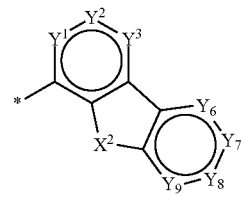

[in the general formula (A5-8), $Y^1$ to $Y^3$, and $Y^6$ to $Y^9$ independently represent =N— or =C($R^3$)— respectively; $R^3$ represents a hydrogen atom or a substituent; at least one of $Y^1$ to $Y^3$ represents =N—; * represents a linkage position to the general formula (A5). $X^2$ represents one member selected from an oxygen atom, a sulfur atom, $NR^2$ or $CR^3R^4$. $R^2$ and $R^4$ are identical to the above described $R^2$ and $R^4$, respectively.]

(Aspect 9)
An organic electroluminescent element described in any one of the aspects 1 to 5. Herein, the nitrogen containing 6 membered heterocycle is a nitrogen-containing 6 membered heterocycle represented by the general formula (A5-1).

General Formula (A5-1)

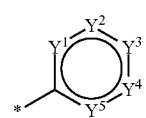

[in the general formula (A5-1), $Y^3$ represents =N—; $Y^1$, $Y^2$, $Y^4$ and $Y^5$ represents =C($R^3$)—; $R^3$ represents a hydrogen atom or a substituent; * represents a linkage position to the general formula (A5). Note, $Y^1$ and $Y^2$, or $Y^4$ and $Y^5$ may be condensed together to form a ring.]
(1)
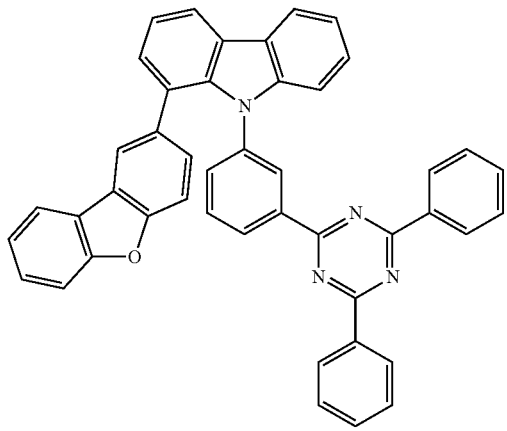
(2)
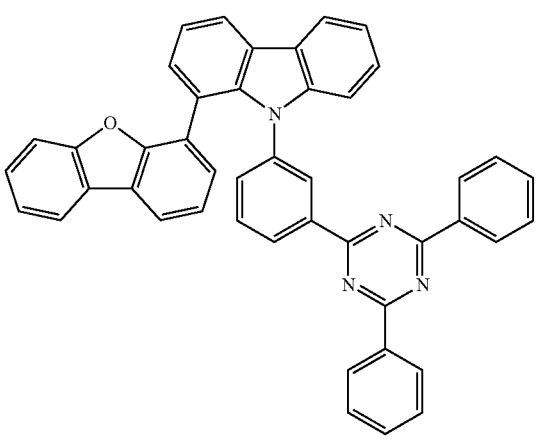
(3)
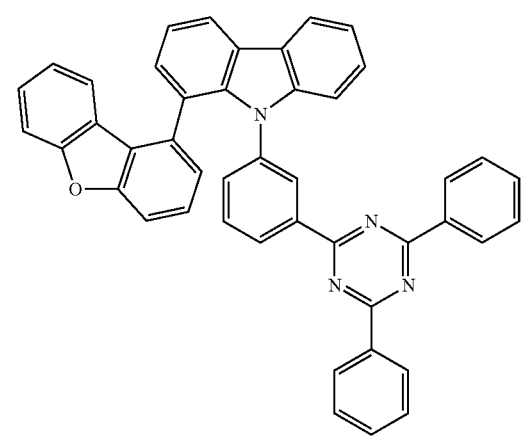
-continued
(4)
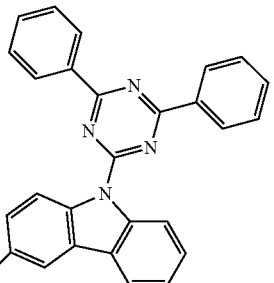
(5)
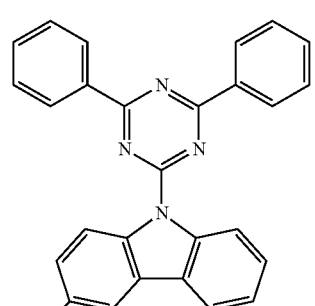
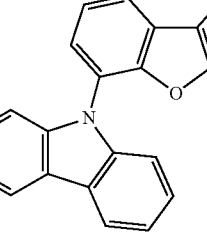
(6)
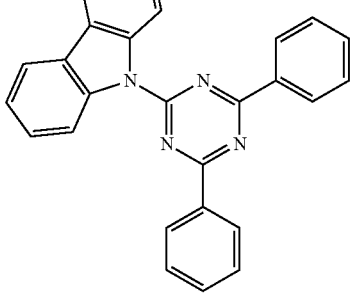

(7)
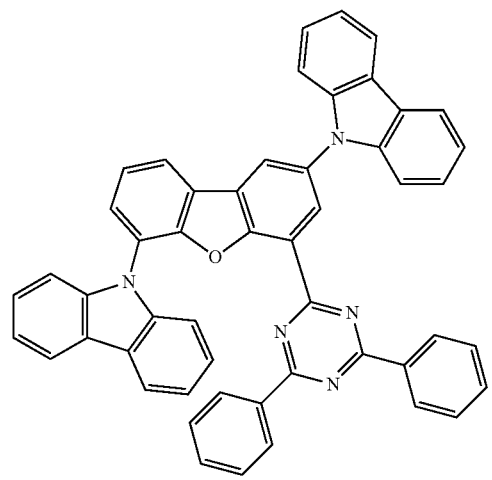
(8)
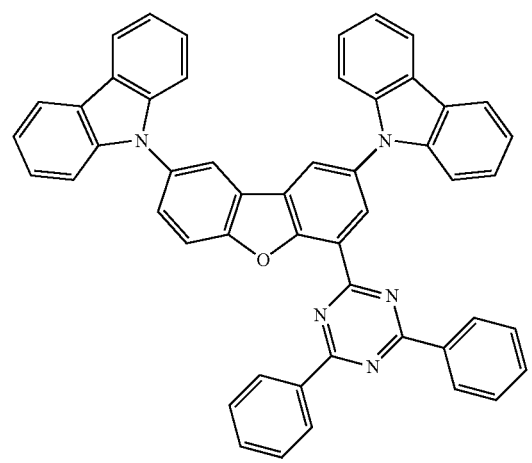
(9)
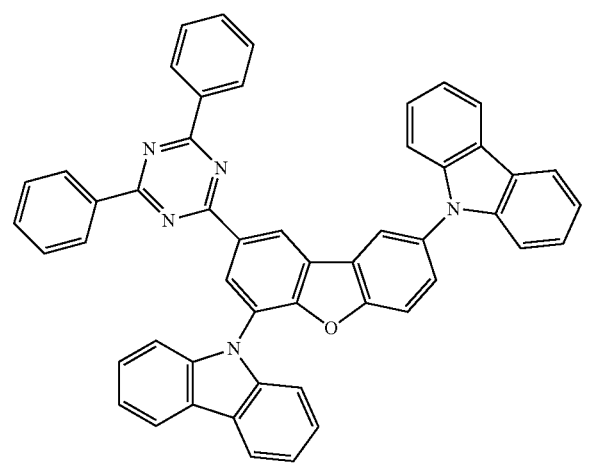
(10)
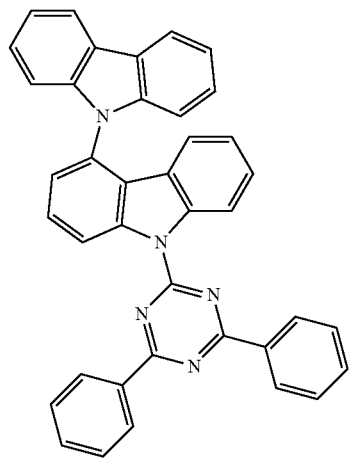
(11)
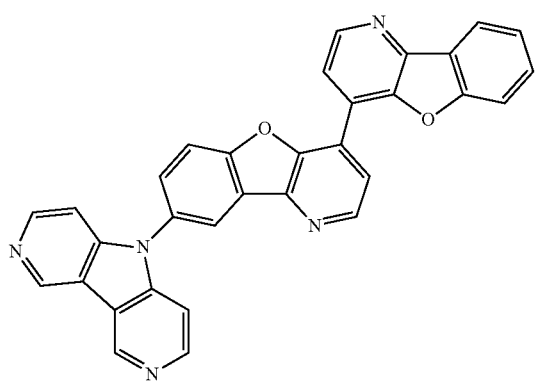
(12)
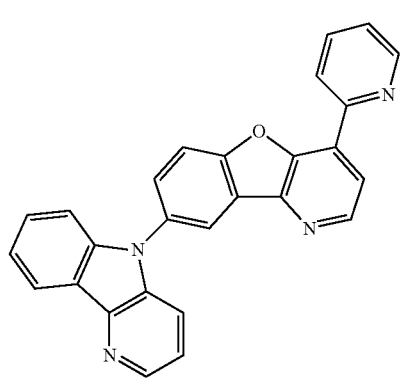
(13)
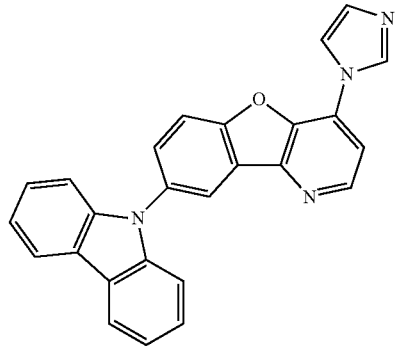

-continued (14)

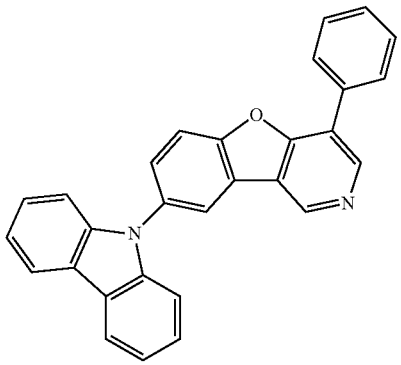

(Aspect 11)

An organic electroluminescent element described in any one of the aspects 1 to 10. Herein, the luminescent layer contains at least one of the compounds represented by the general formulae (A1) to (A5).

(Aspect 12)

An organic electroluminescent element described in any one of the aspects 1 to 11. Herein, the luminescent layer contains a phosphorescent dopant.

(Aspect 13)

An organic electroluminescent element described in the aspect 12. Herein, the phosphorescent dopant is an Ir complex.

(Aspect 14)

An organic electroluminescent element described in any one of the aspects 1 to 13. Herein, the luminescent layer includes an electron transfer layer, and the electron transfer layer contains at least one of the compounds represented by the general formulae (A1) to (A5).

(Aspect 15)

A method for producing an organic electroluminescent element described in any one of the aspects 1 to 14 by a wet process.

(Aspect 16)

A display including an organic electroluminescent element described in any one of the aspects 1 to 14.

(Aspect 17)

A lighting device including an organic electroluminescent element described in any one of the aspects 1 to 14.

According to the above aspects, an organic EL element having high luminescent efficiency, a small aging variation of the luminescent intensity even after storage at a high temperature, and further a long luminescent lifetime at a high temperature may be provided. Further, the producibility in a wet process may be improved. Moreover, a display and a lighting device including the organic EL element of the present invention may be provided.

DETAILED DESCRIPTION OF THE INVENTION

Figure 1:
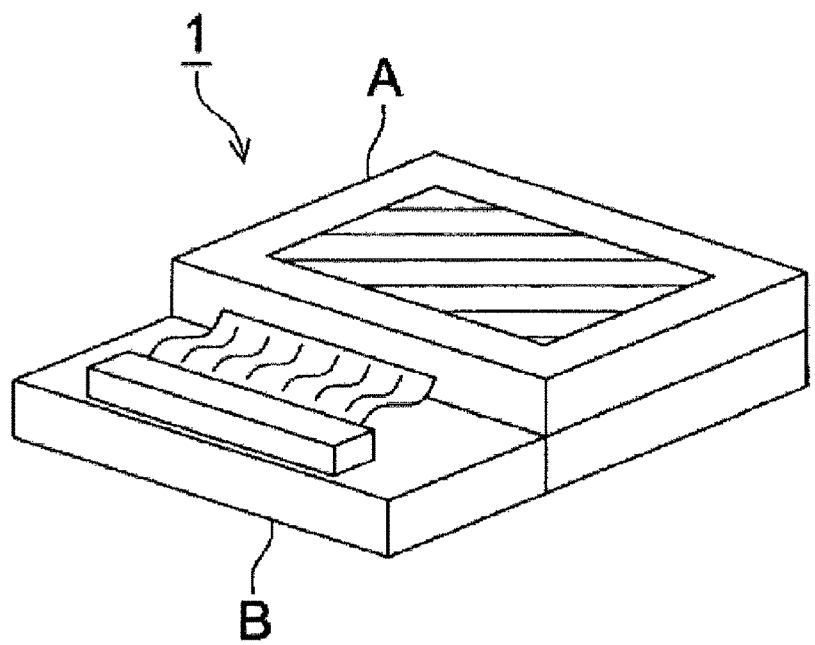
FIG. 1 is a perspective diagram schematically exemplifying a structure of a display of the present invention.

Hereinafter, components of the present invention, and embodiments for carrying out the present invention will be described in detail. Herein, a symbol represented by "~" is used for indicating a range of numeral values so that the numeral values described just before and after the symbol are included in the range, as the upper limit and lower limit values.

Next, embodiments for carrying out the present invention will be described in detail. However, the present invention is not limited to those embodiments.

<<Organic Electroluminescent Element>>

An organic electroluminescent element of the present invention is an element containing at least an organic layer provided between a pair of electrodes (i.e., a cathode and an anode). The organic layer is formed of at least one layer including a luminescent layer, and at least one layer of the organic layer contains at least one of the compounds represented by the following general formulae (A1) to (A5).

[General Formulae (A1) to (A3)]

Compounds represented by the general formulae (A1) to (A3) are the followings.

General Formula (A1)

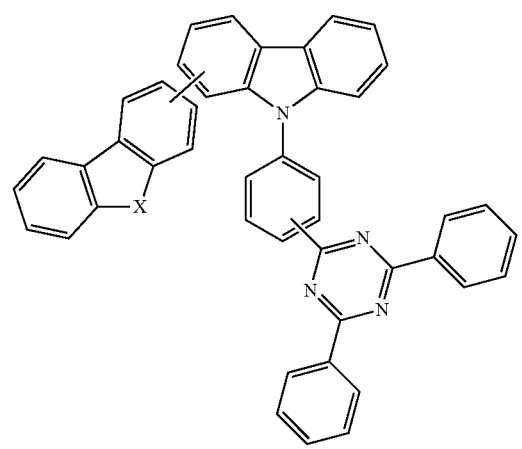

General Formula (A2)

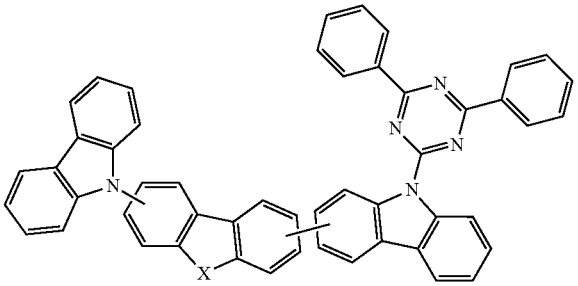

-continued

General Formula (A3)

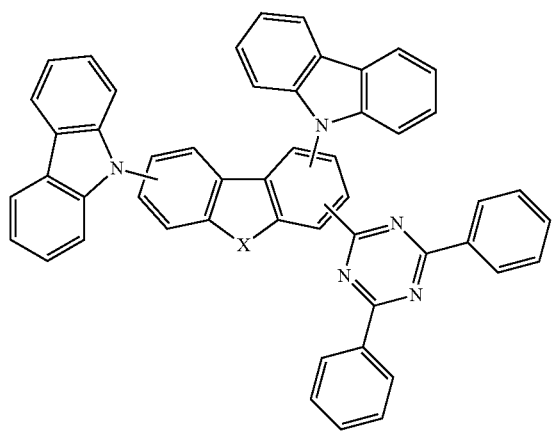

In the general formulae (A1) to (A3), X represents an oxygen atom or a sulfur atom, preferably an oxygen atom.

[General Formula (A4)]
Compounds represented by the general formula (A4) are the followings.

General Formula (A4)

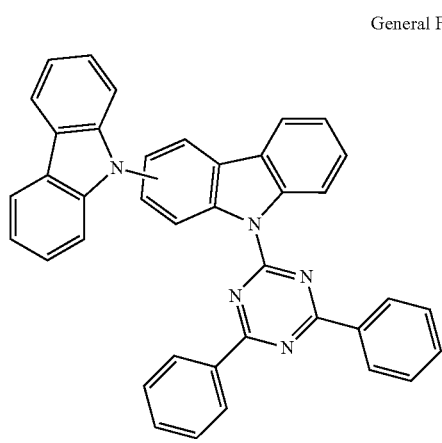

[General Formula (A5)]
Compounds represented by the general formula (A5) are the followings. Hereinafter, the general formula (A5) represented by the following expression is appropriately referred to as general formula (A5-a).

General Formula (A5)

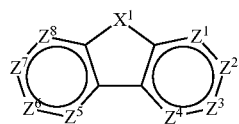

In the general formula (A5), $X^1$ represents an oxygen atom or a sulfur atom, preferably an oxygen atom.

[in the general formula (A5), $Z^1$ to $Z^8$ independently represent =N— or =C($R^1$)—; $R^1$ represents a hydrogen atom or a substituent; at least one of $Z^1$ to $Z^4$ represents =N—. Note, when $Z^4$ is =N—, $Z^1$ represents =N— or =C($R^2$)—, and $R^2$ represents a nitrogen-containing 6 membered heterocycle of the following general formula (A5-1) or a nitrogen-containing 5 membered ring of the following general formula (A5-2). Further, when $Z^4$ is =C($R^1$)—, at least $Z^3$ represents =N—.]

[General Formula (A5-1)]
Compounds represented by the general formula (A5-1) are the followings.

General Formula (A5-1)

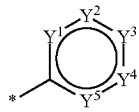

[in the general formula (A5-1), $Y^1$ to $Y^5$ independently represent =N— or =C($R^3$)— respectively; $R^3$ represents a hydrogen atom or a substituent; at least one of $Y^1$ to $Y^5$ represents =N—; * represents a linkage position to the structure of the general formula (A5). Note, when two of =C($R^3$)— are adjacently placed in series, two of $R^3$ may be condensed together to form a ring. Particularly, when $Y^1$ or $Y^4$ represents =N— and two of =C($R^3$)— are adjacently placed in series, preferably two of $R^3$ are condensed together to form a ring.]

[General Formula (A5-2)]
Compounds represented by the general formula (A5-2) are the followings.

General Formula (A5-2)

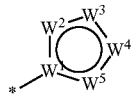

[in the general formula (A5-2), $W^1$ represents —N— or =C—; $W^2$ to $W^5$ independently represent =N— or =C($R^4$)— respectively; $R^4$ represents a hydrogen atom or a substituent; at least one of $W^1$ to $W^5$ represents =N—; * represents a linkage position to the structure of the general formula (A5). Note, when two of =C($R^4$)— are adjacently placed in series, two of $R^4$ may be condensed together to form a ring.

Further, in the organic electroluminescent element of the present invention, at least one layer forming the organic layer may contain at least one of the compounds represented by the general formulae (A1) to (A4) and the general formula (A5) (hereinafter, the general formula (A5) represented by general formula (A5-a) is appropriately referred to as general formula (A5-b). That is, compounds represented by the general formula (A5-b) may be contained instead of compounds represented by the general formula (A5-a). Moreover, the compounds represented by the general formula (A5-b) as well as the compounds represented by the general formula (A5-a) may be contained.

Furthermore, expression of the compounds represented by the general formula (A5-a) (for example, expression of $Z^1$ to $Z^8$) may be further limited to the expression of the compounds represented by the general formula (A5-b).

General Formula (A5)

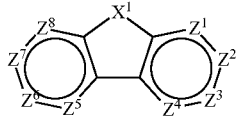

[in the general formula (A5), $X^1$ represents an oxygen atom or a sulfur atom, preferably an oxygen atom.]

[in the general formula (A5), $Z^1$ to $Z^8$ independently represent =N— or =C($R^1$)—, $R^1$ represents a hydrogen atom or a substituent, at least one of $Z^1$ to $Z^4$ represents =N— and remaining ones of $Z^1$ to $Z^4$ represent =C($R^1$)—, at least one of $R^1$ in the remaining ones of $Z^1$ to $Z^4$ represents a nitrogen-containing 6 membered heterocycle of the following general formula (A5-1).]

General Formula (A5-1)

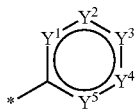

[in the general formula (A5-1), $Y^1$ to $Y^5$ independently represent =N— or =C($R^3$)— respectively; $R^3$ represents a hydrogen atom or a substituent; at least one of $Y^1$ to $Y^5$ represents =N—; * represents a linkage position to the structure of the general formula (A5). Note, when two of =C($R^3$)— are adjacently placed in series, two of $R^3$ may be condensed together to form a ring. Particularly, when $Y^1$ or $Y^4$ represents =N— and two of =C($R^3$)— are adjacently placed in series, preferably two of $R^3$ are condensed together to form a ring.]

Further, in the organic electroluminescent element of the present invention, at least one layer forming the organic layer may contain at least one of the compounds represented by the general formulae (A1) to (A4) and the general formula (A5) (hereinafter, the general formula (A5) represented by the following expression is appropriately referred to as general formula (A5-c). That is, compounds represented by the general formula (A5-c) may be contained instead of compounds represented by the general formula (A5-a). Moreover, the compounds represented by the general formula (A5-b) as well as the compounds represented by the general formula (A5-a) may be contained.

Furthermore, expression of the compounds represented by the general formula (A5-a) or (A5-b) (for example, expression of $Z^1$ to $Z^8$) may be further limited to the expression of the compounds represented by the general formula (A5-c).

General Formula (A5)

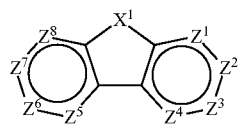

[in the general formula (A5), $X^1$ represents an oxygen atom or a sulfur atom, preferably an oxygen atom.]

[in the general formula (A5), $Z^1$ to $Z^3$ represent =C($R^1$)—, $Z^4$ represents =N—, $Z^5$ to $Z^8$ independently represent =N— or =C($R^1$)— respectively, $R^1$ represents a hydrogen atom or a substituent, at least one of $R^1$ in $Z^1$ to $Z^3$ represents a nitrogen-containing 6 membered heterocycle of the following general formula (A5-1).]

General Formula (A5-1)

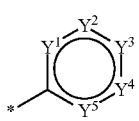

[in the general formula (A5-1), $Y^1$ to $Y^5$ independently represent =N— or =C($R^3$)— respectively, $R^3$ represents a hydrogen atom or a substituent, at least one of $Y^1$ to $Y^5$ represents =N—, * represents a linkage position to the general formula (A5). Note, when two of =C($R^3$)— are adjacently placed in series, two of $R^3$ may be condensed together to form a ring. Particularly, when $Y^1$ or $Y^4$ represents =N— and two of =C($R^3$)— are adjacently placed in series, preferably two of $R^3$ are condensed together to form a ring.]

Further, the general formula (A5-1) may be represented by the following general formula (A5-3) or (A5-4).

General Formula (A5-3)

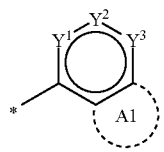

[in the general formula (A5-3), $Y^1$ to $Y^3$ independently represent =N— or =C($R^3$)— respectively; $R^3$ represents a hydrogen atom or a substituent; at least one of $Y^1$ to $Y^3$ represents =N—; * represents a linkage position to the general formula (A5). A1 represents a residue forming a 6 membered aryl, 6 membered heteroaryl or 5 membered heteroaryl ring.]

General Formula (A5-4)

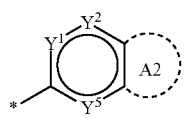

[in the general formula (A5-4), $Y^1$, $Y^2$ and $Y^5$ independently represent =N— or =C($R^3$)— respectively; $R^3$ represents a hydrogen atom or a substituent; at least one of $Y^1$, $Y^2$ and $Y^5$ represents =N—; * represents a linkage position to the general formula (A5). A2 represents a residue forming a 6 membered aryl, 6 membered heteroaryl or 5 membered heteroaryl ring.]

Further, the general formula (A5-1) is represented by the general formula (A5-4), and the general formula (A5-4) may be represented by the following general formula (A5-5) or (A5-6).

General Formula (A5-5)

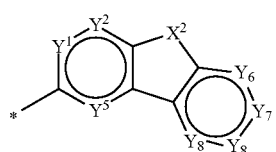

[in the general formula (A5-5), $Y^1$, $Y^2$, and $Y^5$ to $Y^9$ independently represent =N— or =C($R^3$)— respectively; $R^3$ represents a hydrogen atom or a substituent; at least one of $Y^1$, $Y^2$ and $Y^5$ represents =N—; * represents a linkage position to the general formula (A5). $X^2$ represents one member selected from an oxygen atom, a sulfur atom, $NR^2$ or $CR^3R^4$. $R^2$ and $R^4$ are identical to the above described $R^2$ and $R^4$, respectively.]

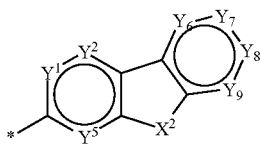

General Formula (A5-6)

[in the general formula (A5-6), $Y^1$, $Y^2$, and $Y^5$ to $Y^9$ independently represent =N— or =C($R^3$)— respectively; $R^3$ represents a hydrogen atom or a substituent; at least one of $Y^1$, $Y^2$ and $Y^5$ represents =N—; * represents a linkage position to the general formula (A5). $X^2$ represents one member selected from an oxygen atom, a sulfur atom, $NR^2$ or $CR^3R^4$. $R^2$ and $R^4$ are identical to the above described $R^2$ and $R^4$, respectively.]

The general formula (A5-1) is represented by the general formula (A5-3), and the general formula (A5-3) may be represented by the following general formula (A5-7) or (A5-8).

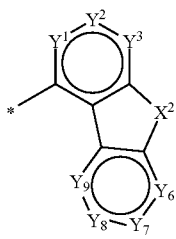

General Formula (A5-7)

[in the general formula (A5-7), $Y^1$ to $Y^3$, and $Y^6$ to $Y^9$ independently represent =N— or =C($R^3$)— respectively; $R^3$ represents a hydrogen atom or a substituent; at least one of $Y^1$ to $Y^3$ represents =N—; * represents a linkage position to the general formula (A5). $X^2$ represents one member selected from an oxygen atom, a sulfur atom, $NR^2$ or $CR^3R^4$. $R^2$ and $R^4$ are identical to the above described $R^2$ and $R^4$, respectively.]

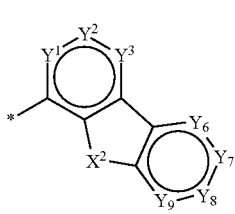

General Formula (A5-8)

[in the general formula (A5-8), $Y^1$ to $Y^3$, and $Y^6$ to $Y^9$ independently represent =N— or =C($R^3$)— respectively; $R^3$ represents a hydrogen atom or a substituent; at least one of $Y^1$ to $Y^3$ represents =N—; * represents a linkage position to the general formula (A5). $X^2$ represents one member selected from an oxygen atom, a sulfur atom, $NR^2$ or $CR^3R^4$. $R^2$ and $R^4$ are identical to the above described $R^2$ and $R^4$, respectively.]

The nitrogen-containing 6 membered heterocycle in the general formula (A5) (i.e., the general formulae (A5-a), (A5-b) and (A5-c)) may be a nitrogen-containing 6 membered heterocycle represented by the general formula (A5-1).

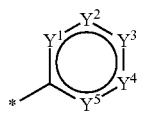

General Formula (A5-1)

[in the general formula (A5-1), $Y^3$ represents =N—; $Y^1$, $Y^2$, $Y^4$ and $Y^5$ represents =C($R^3$)—; $R^3$ represents a hydrogen atom or a substituent; * represents a linkage position to the general formula (A5). $Y^1$ and $Y^2$, or $Y^4$ and $Y^5$ may be condensed together to form a ring.]

A substituent represented by $R^1$, $R^3$ and $R^4$ includes, for example, an alkyl group such as a methyl group, an ethyl group, a propyl group, an isopropyl group, a tert-butyl group, a pentyl group, a hexyl group, an octyl group, a dodecyl group, a tridecyl group, a tetradecyl group, a pentadecyl group; a cycloalkyl group such as a cyclopentyl group, cyclohexyl group; an alkenyl group such as a vinyl group, an allyl group; an alkynyl group such as an ethynyl group, propargyl group; an aromatic hydrocarbon group (or called an aromatic hydrocarbon ring group, an aromatic ring group or an aryl group) such as a phenyl group, p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, a biphenyl group; an aromatic heterocyclic group such as a pyridyl group, a pyrazyl group, a pyrimidinyl group, a triazyl group, a furyl group, a pyrrolyl group, an imidazolyl group, a benzoimidazolyl group, a pyrazolyl group, a pyrazinyl group, a triazolyl group (e.g., 1,2,4-triazole-1-yl group, a 1,2,3-triazol-1-yl group, an oxazolyl group, a benzoxazol group, a triazolyl group, an isoxazolyl group, an isothiazolyl group, a furazanyl group, a thienyl group, a quinolyl group, a benzofuryl group, dibenzofuryl group, a dibenzofuryl group in which at least one of carbon atoms is replaced by a nitrogen atom such as azadibenzofuryl group, diazabenzofuryl group, a benzothienyl group, dibenzothienyl group, dibenzothienyl group in which at least one of carbon atoms is replaced by a nitrogen atom such as azadibenzothienyl group, diazabenzothienyl group, indolyl group, a carbazolyl group, a carbazolyl group in which at least one of carbon atoms is replaced by a nitrogen atom such as azacarbazolyl group, diazacarbazolyl group, quinoxalinyl group, a pyridazinyl group, a triazinyl group, a quinazolinyl group, a phtharazinyl group; a heterocyclic group such as a pyrrolidyl group, an imidazolidyl group, a morpholyl group, an oxazolidyl group; an alkoxy group such as a methoxy group, an ethoxy group, a propyloxy group, a pentyloxy group, a hexyloxy group, an octyloxy group, a dodecyloxy group; a cycloalkoxy group such as a cyclopentyloxy group, a cyclohexyloxy group; an aryloxy group such as a phenoxy group, a naphthyloxy group; an alkylthio group such as a methylthio group, an ethylthio group, a propylthio group, a pentylthio group, a hexylthio group, an octylthio group, a dodecylthio group; a cycloalkylthio group such as cyclopentylthio group, a cyclohexylthio group; an arylthio group such as a phenylthio group, a naphthylthio group; an alkoxycarbonyl group such as a methyloxycarbonyl group, a butyloxycarbonyl group, an octyloxycarbonyl group, a dodecyloxycarbonyl group; an aryloxycarbonyl group such as phenyloxycarbonyl group, a naphthyloxycarbonyl group; a sulfamoyl group such as an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, a 2-pyridylaminosulfonyl group; an acyl group such as an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, a pyridylcarbonyl group; an acyloxy group such as an acetyloxy group, ethylcarbonyloxy group, a butylcarbonyloxy group, an octylcarbonyloxy group, a dodecylcarbonyloxy, a phenylcarbonyloxy; an amide group such as a methylcarbonylamino group, an ethylcarbonylamino group, a dimethylcarbonylamino group, a propylcarbonylamino group, a pentylcarbonylamino group, a cyclohexylcarbonylamino, a 2-ethylhexylcarbonylamino group, an octylcarbonylamino group, a dodecylcarbonylamino group, a phenylcarbonylamino group, a naphthylcarbonylamino group; a carbamoyl group such as an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, a 2-pyridylaminocarbonyl group; a ureide group such as a methylureide group, an ethylureide group, a pentylureide group, a cyclohexylureide group, an octylureide group, a dodecylureide group, a phenylureide group, a naphthylureide group, a 2-pyridylaminoureide group; a sulfinyl group such as a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, a 2-pyridylsulfinyl group; an alkylsulfonyl group such as a methylsulfonyl group, an ethylsulfonyl group, a butylsulfonyl group, a cyclohexylsulfonyl group, a 2-ethylhexylsulfonyl group, a dodecylsulfonyl group; an arylsulfonyl group or a heteroarylsulfonly group such as a phenylsulfonlyl group, a naphthylsulfonyl group, a 2-pyridinylsulfonyl group; an amino group such as an amino group, an ethylamino group, a dimethylamino group, a butylamino group, a cyclopentylamino group, a 2-ethylhexylamino group, a dodecylamino group, an anilino group, a naphthylamino group, a 2-pyridylamino group; a halogen atom such as a fluorine atom, a chlorine atom, a bromine atom; a fluorohydrocarbon group such as a fluoromethyl group, a trifluoromethyl group, a pentafluoroethyl group, a pentafluorophenyl; a cyano group, a nitro group, a hydroxy group, a mercapto group, group, a silyl group such as a trimethylsilyl group, a triisopropylsilyl group, a triphenylsilyl group, a phenyldiethylsilyl group, and a phosphono group or the like. Note, the substituents represented by $R^1$, $R^3$ and $R^4$ are not limited to the above examples.

The substituents may be further substituted with the above described substituents, and moreover the plurality of substituents may be bonded together to form a ring structure.

Among the substituents represented by $R^1$, $R^3$ and $R^4$, a preferable substituent is an alkyl group, an aromatic hydrocarbon group and an aromatic heterocyclic group, and a most preferable one is an aromatic hydrocarbon group and an aromatic heterocyclic group.

Next, specific examples of the compounds represented by the general formulae (A1) to (A5) will be described below. However, the compounds are not limited to those specific examples. Note, a skilled person in the art may synthesize those compounds by conventionally known methods.

(1)

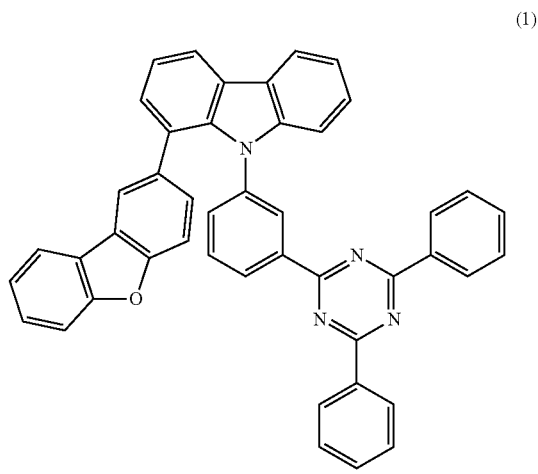

(2)

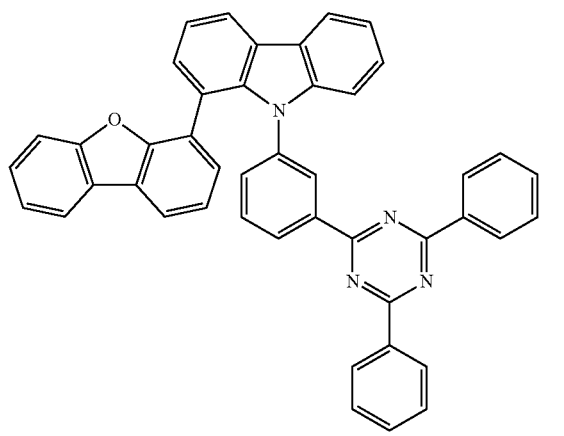

(3)

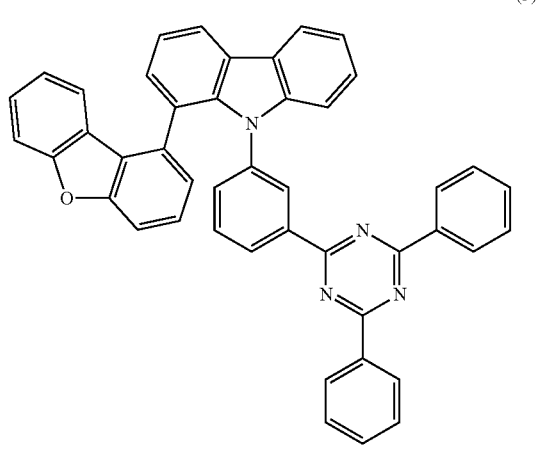

(4)
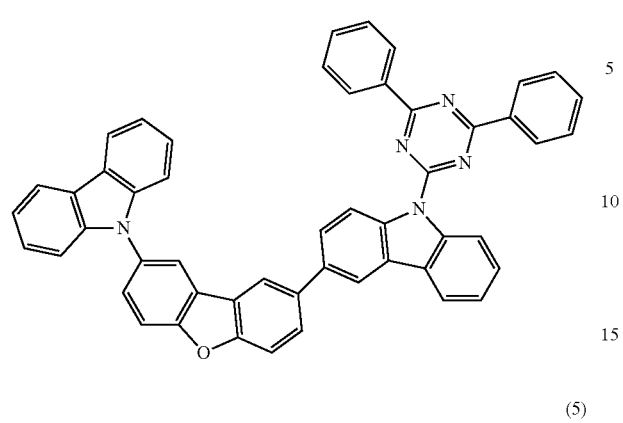
(5)
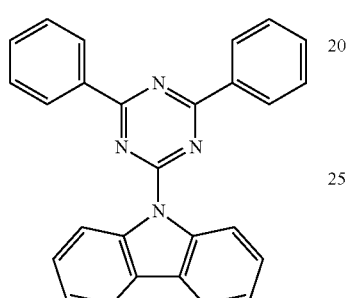
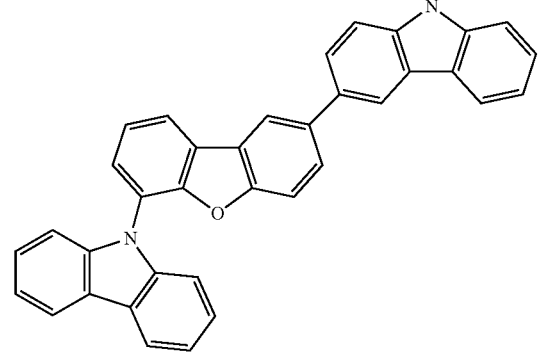
(6)
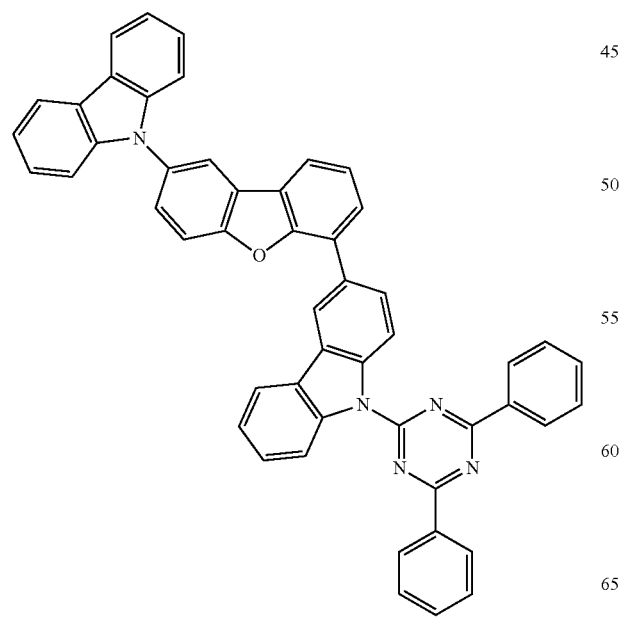
(7)
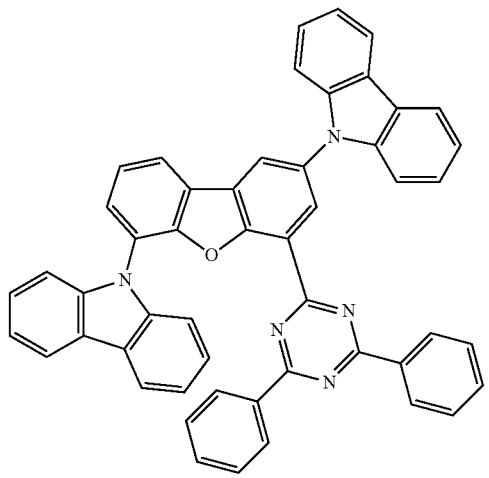
(8)
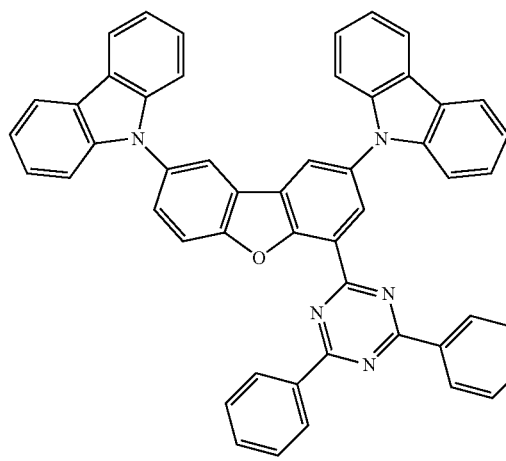
(9)
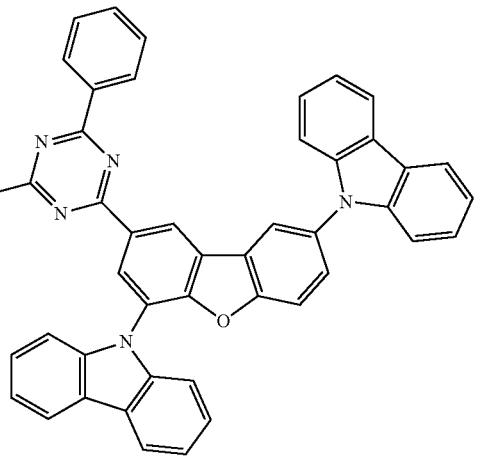

(10)
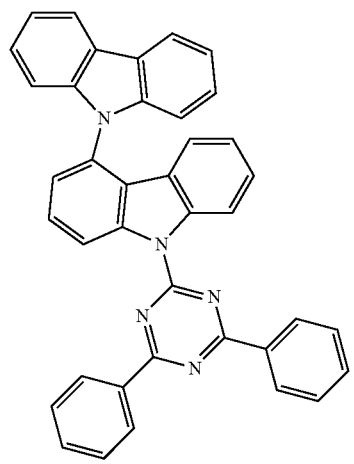
(11)
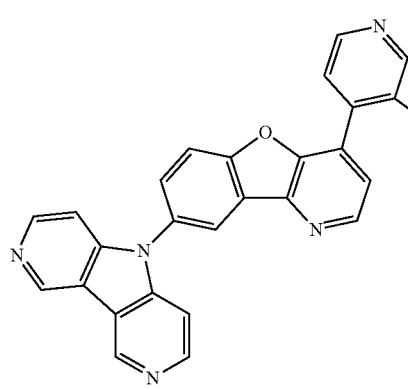
(12)
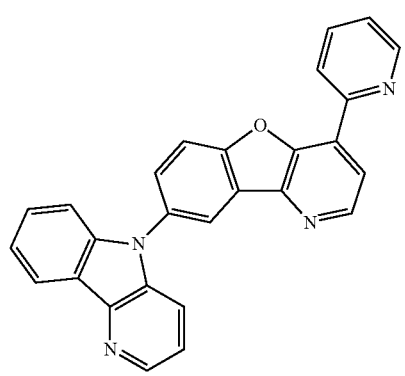
(13)
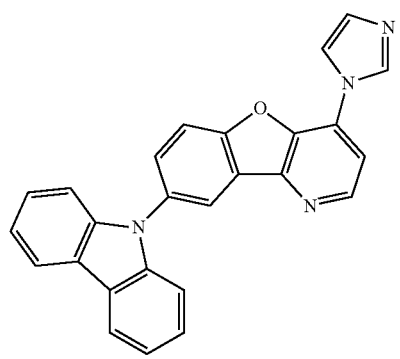
(14)
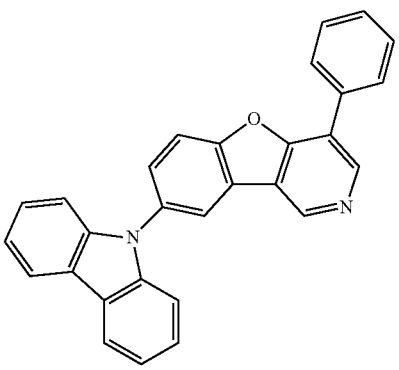
A5-1
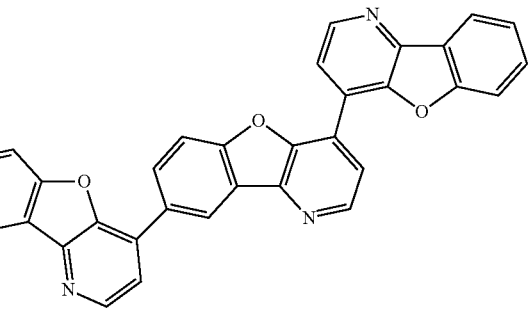
A5-2
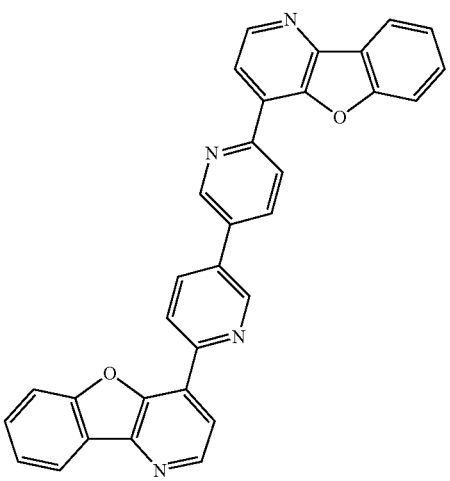
A5-3
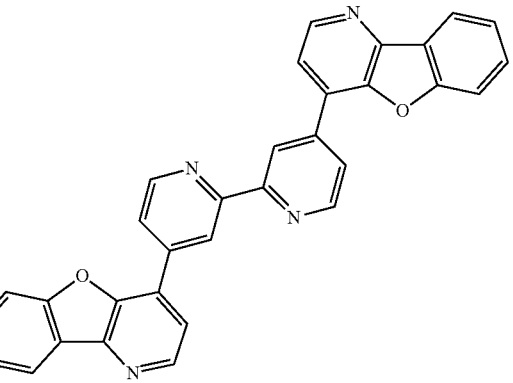

A5-4
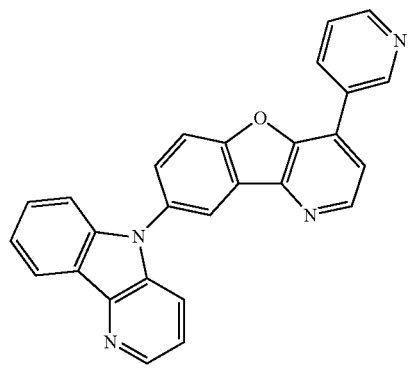
A5-5
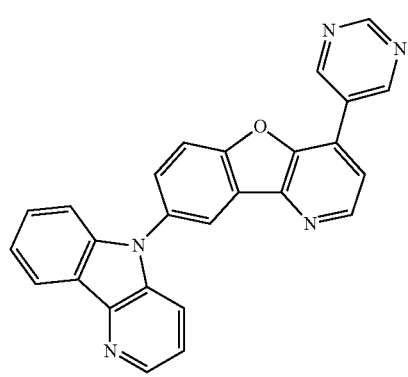
A5-6
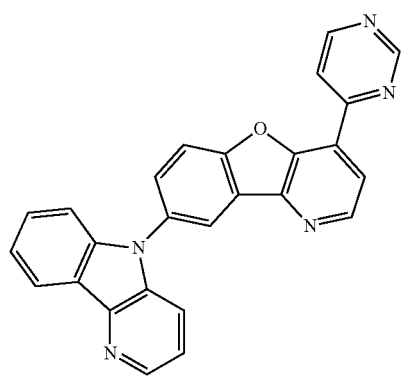
A5-7
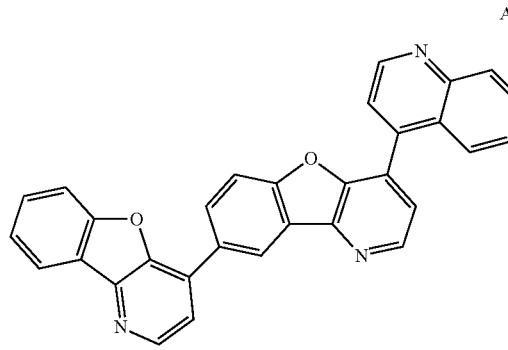
A5-8
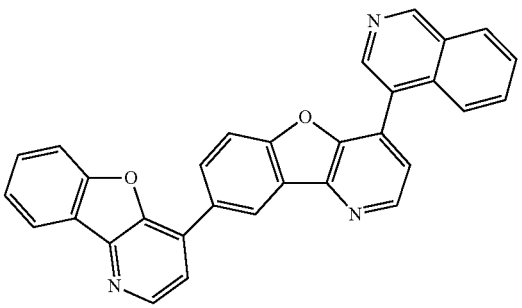
A5-9
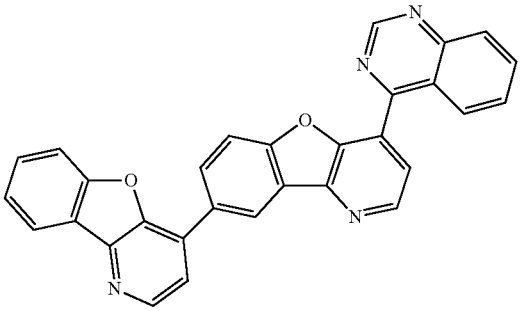
A5-10
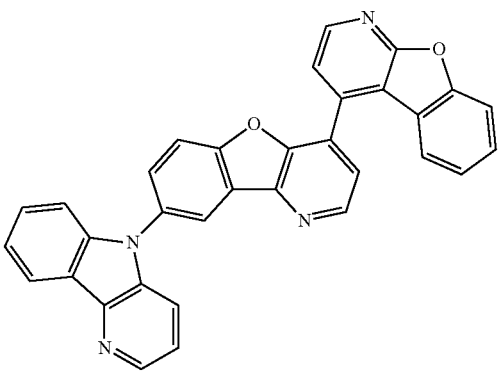
A5-11
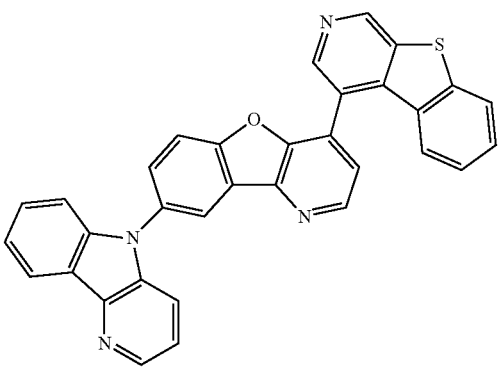

A5-12
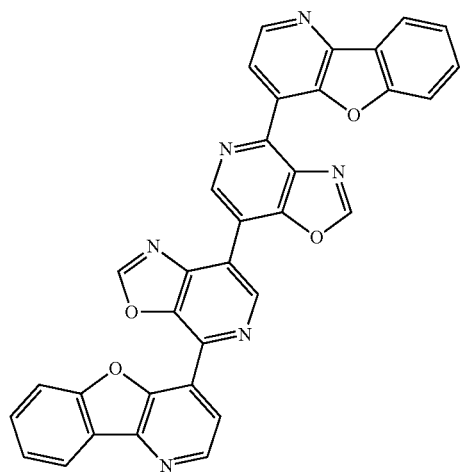
A5-13
A5-14
A5-15
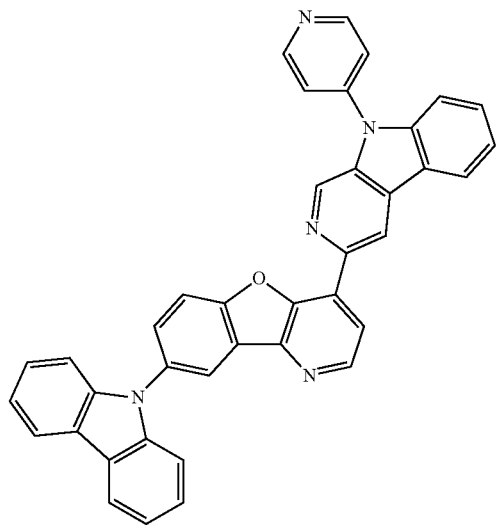
A5-16
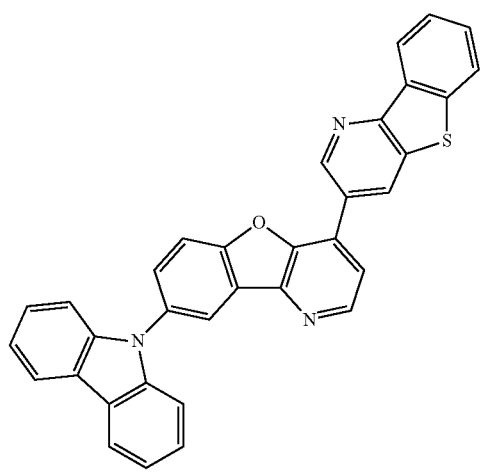
A5-17
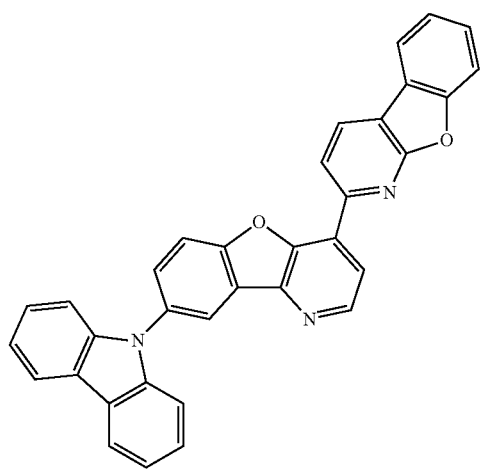

A5-18
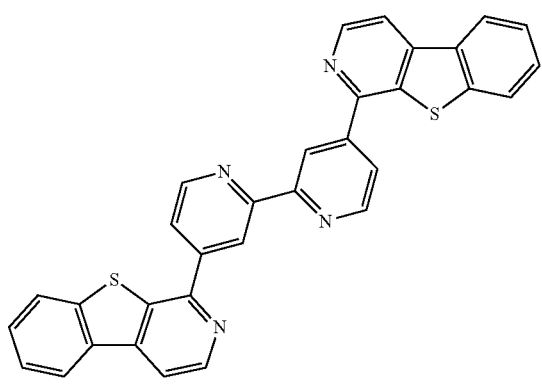
A5-19
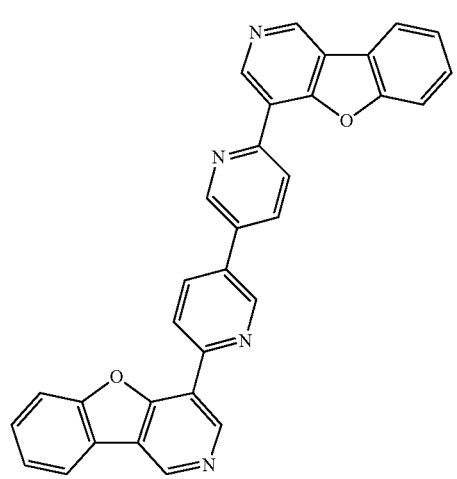
A5-20
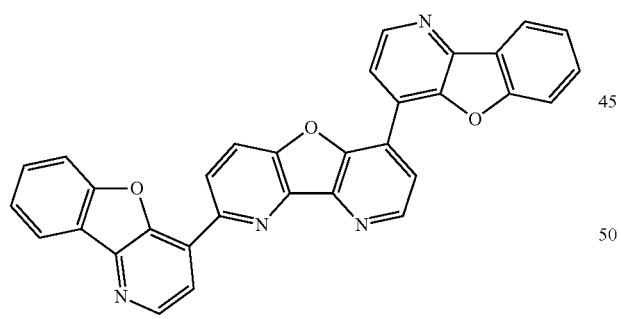
A5-21
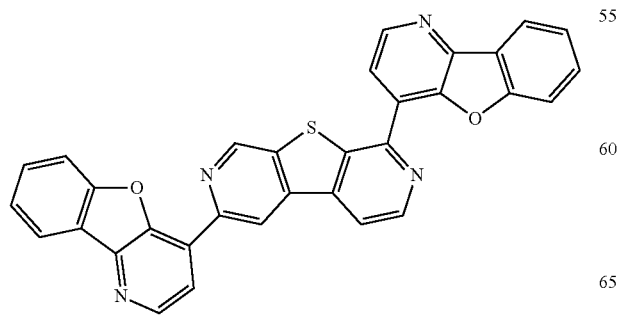
A5-22
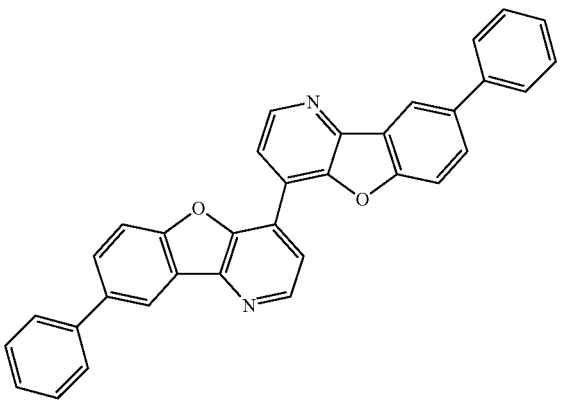
A5-23
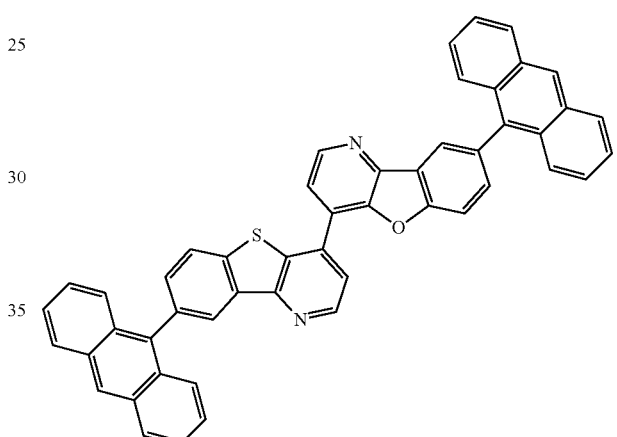
A5-24
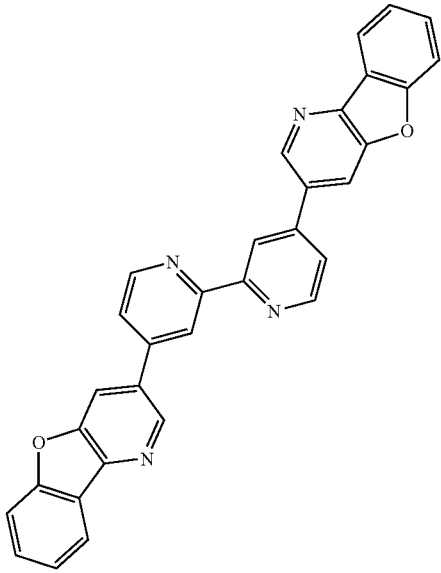

A5-25
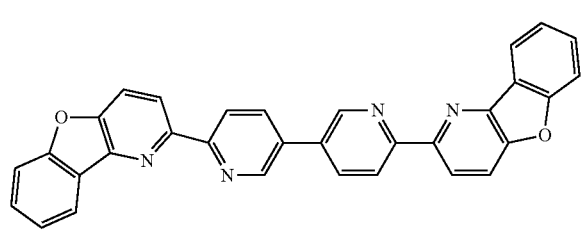

A5-26
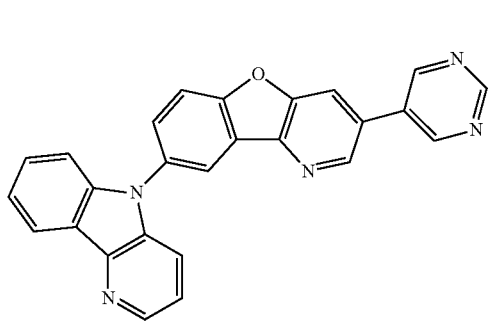

A5-27
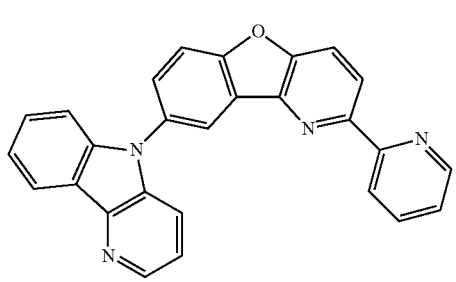

A5-28
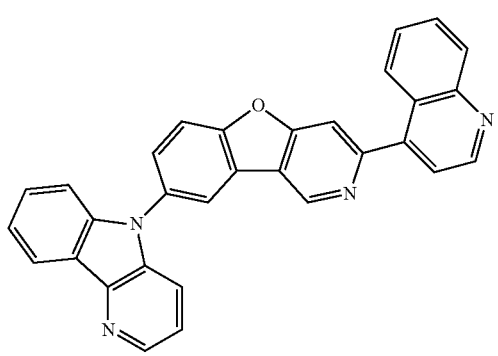

A5-29
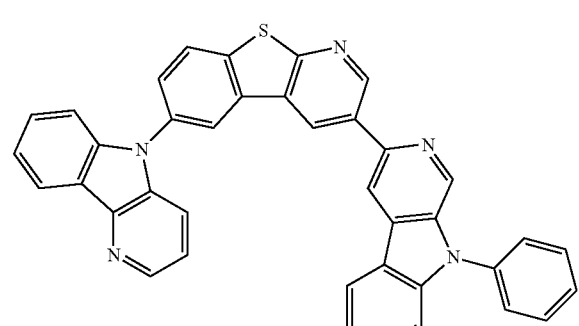

A5-30
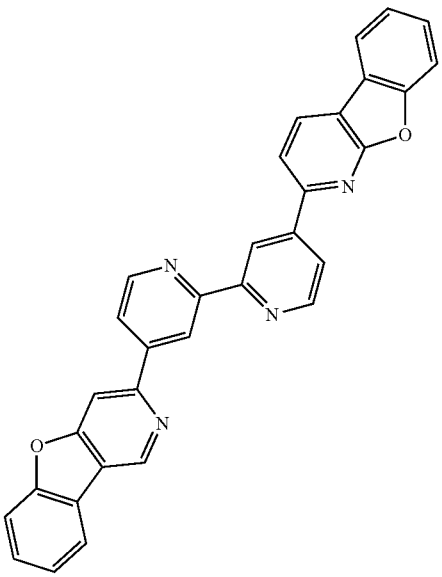

A5-31

In the present invention, the luminescent layer preferably contains at least one selected from the compounds represented by the general formulae (A1) to (A5). Further, the luminescent layer preferably contains at least one of the compounds represented by the general formulae (A1) to (A5) as a host compound. Note, the luminescent layer preferably contains a phosphorescent dopant. Further, the phosphorescent dopant is preferably an Ir complex. Here, in addition to the compounds represented by the general formulae (A1) to (A5), preferably the luminescent layer further contains a host compound having a different structure therefrom (i.e., a known host compound). A detailed structure and composition of the luminescent layer as well as the host compound having a different structure from the compounds represented by the general formulae (A1) to (A5) will be described later.

Further, in the present invention, preferably the organic layer includes an electron transfer layer, and the electron transfer layer preferably contains at least one of the compounds represented by the general formulae (A1) to (A5). When the electron transfer layer contains one of the compounds represented by the general formulae (A1) to (A5), the organic EL element of the present invention may have the following properties: high luminescent efficiency, a small aging variation of the luminescent even after storage at a high temperature, and a long luminescent lifetime at a high temperature. Moreover, the organic EL element of the present invention may be driven at a low voltage with small rise of voltage at driving.

As mentioned above, both the luminescent layer and the electron transfer layer contain at least one selected from the compounds represented by the general formulae (A1) to (A5).

Preferably, azadibenzofuran derivatives represented by the general formula (A5) (i.e., general formulae (A5-a), (A5-b) and (A5-c)) of the present invention are used especially for a layer which transfers electrons. That is, such a layer is preferably provided between a luminescent layer and a cathode, and is used for, for example, an electron transfer layer and an electron injection layer and the like.

Azadibenzofuran is a compound formed by introducing a nitrogen atom into a dibenzofuran skeleton having a large π plane suitable for transferring electrons. Introduction of a nitrogen atom having high electronegativity affords the following advantages: 1) the LUMO level is lowered; and 2) the intermolecular hopping is increased due to interaction between n-electron and π-electron located on the nitrogen atom. Further, when an aromatic heterocyclic ring represented by the general formula (A5) of the compound contained in the organic layer is replaced with a freely-rotatable single bond, LUMO distribution thereof is to be extended over the azadibenzofuran skeleton and aromatic heterocyclic rings of the compound. This extension of the LUMO distribution enables 1) the LUMO level is to be further lowered; and 2) the intramolecular hopping is kept even when the element is stored at a high temperature.

This is because when the azadibenzofuran skeleton is bonded to the aromatic heterocyclic ring via a freely-rotatable single bond, the electron hopping may be kept even when a film property is slightly changed. This feature prevents deterioration of the lifetime and rise of the drive voltage from being caused even when the drive voltage is lowered and the element is stored at a high temperature.

<<Layers Structuring Organic EL Element>>

Next, representative element structures of the organic EL element of the present invention are listed as follows. However, the present invention is not limited to those structures.

(1) Anode/Luminescent Layer/Cathode (2) Anode/Luminescent Layer/Electron Transfer Layer/Cathode (3) Anode/Hole Transfer Layer/Luminescent Layer/Cathode (4) Anode/Hole Transfer Layer/Luminescent Layer/Electron Transfer Layer/Cathode (5) Anode/Hole Transfer Layer/Luminescent Layer/Electron Transfer Layer/Electron Injection Layer/Cathode (6) Anode/Hole Injection Layer/Hole Transfer Layer/Luminescent Layer/Electron Transfer Layer/Cathode (7) Anode/Hole Injection Layer/Hole Transfer Layer/(Electron Blocking Layer/) Luminescent Layer/(Hole Blocking Layer/)Electron Transfer Layer/Electron Injection Layer/Cathode Among the above structures, the structure (7) is preferably used. However, the present invention is not limited to the structure (7).

The luminescent layer of the present invention is formed of a single layer or a plurality of layers. In case of a plurality of layers, an intermediate layer (i.e., non-luminescent layer) may be provided between the luminescent layers, respectively.

Where necessary, a hole blocking layer (or called a hole barrier layer) or an electron injection layer (or called cathode buffer layer) may be provided. Alternatively, an electron blocking layer (or called electron barrier layer) or a hole injection layer (or called anode buffer layer) may be provided between the luminescent layer and the anode.

An electron transfer layer used in the present invention is a layer having a function for transferring electrons. Therefore, in a board sense, an electron injection layer and a hole blocking layer are also included in the electron transfer layer. Herein, the electron transfer layer may be formed of a plurality of layers.

A hole transfer layer used in the present invention is a layer having a function for transferring holes. Therefore, in a board sense, a hole injection layer and an electron blocking layer are also included in the hole transfer layer. Herein, the hole transfer layer may be formed of a plurality of layers.

In the above representative structures of the element, a layer other than the anode and cathode is called an "organic layer".

(Tandem Structure)

Further, the organic EL element of the present invention may be an element having a so-called tandem structure in which a luminescent units including at least one luminescent layer is repeatedly stacked one another.

Next, representative structures of the element having a tandem structure are listed as follows.

Anode/First Luminescent Unit/Second Luminescent Unit/Third Luminescent Unit/Cathode Anode/First Luminescent Unit/Intermediate Layer/Second Luminescent Unit/Intermediate Layer/Third Luminescent Unit/Cathode Here, the first luminescent unit, the second luminescent unit and the third luminescent unit may be the same or different each other. Further, two of the luminescent units may be the same, while the remaining one may be different from the two units Here, the third luminescent unit may be omitted, while a light luminescent unit or an intermediate layer may be further provided between the third luminescent unit and an electrode.

The plurality of luminescent layers may be directly stacked as they are, or stacked via an intermediate layer. The intermediate layer is generally called an intermediate electrode, an intermediate conductive layer, a charge generation layer, an electron withdrawing layer, a contact layer, or an intermediate insulation layer. Herein, when a layer has functions for feeding electrons to an adjacent layer located at the anode side, and simultaneously for feeding holes to an adjacent layer located at the cathode side, known materials and structures are usable for the intermediate layer.

A material used for the intermediate layer includes, for example, a conductive inorganic compound layer such as ITO (indium-tin oxide), IZO (indium-zinc oxide), ZnO2, TiN, ZrN, HfN, TiOx, VOx, CuI, InN, GaN, CuAlO2, CuGaO2, SrCu2O2, LaB6, RuO2, Al; a two-layer film such as Au/Bi2O3; a multilayer film such as SnO2/Ag/SnO2, ZnO/Ag/ZnO, Bi2O3/Au/Bi2O3, TiO2/TiN/TiO2, TiO2/ZrN/TiO2; fullerenes such as C60; a conductive organic substance layer such as oligothiophene; or a conductive organic compound layer such as metallophthalocyanines, non-metallophthalocyanine, metalloporphyrin, non-metalloporphyrin. Note, the present invention is not limited to the above examples.

A preferable structure of the luminescent unit includes, for example, the structures (1) to (7) described above as representative examples from which the anode and cathode are omitted. However, the present invention is not limited to those structures.

Next, specific examples of the tandem organic EL element include, for example, such structures and materials of the element as disclosed in U.S. Pat. Nos. 6,337,492, 7,420,203, 6,107,734, 6,337,492, WO2005/009087, Japanese unexamined patent application publication Nos. 2006-228712, 2006-24791, 2006-49393, 2006-49394, 2006-49396, 2011-96679, 2005-340187, Japanese Patent Nos. 4711424, 3496681, 3884564, 4213169, Japanese unexamined patent application publication Nos. 2010-192719, 2009-076929, 2003-272860, 2003-045676, and WO2005/094130. However, the present invention is not limited to those examples.

Hereinafter, the respective layers forming the organic EL element of the present invention will be described in detail.

<<Luminescent Layer>>

A luminescent layer of the present invention is a layer which provides a field emitting light via excitons generated by recombination of electrons and holes injected from the electrode or the adjacent layer. A luminescent portion thereof may be the inside of the luminescent layer or an interface between the luminescent layer and the adjacent layer. Note, a structure of the luminescent layer used in the present invention is not specifically limited so long as the luminescent layer satisfies the requirements defined in the present invention.

A total thickness of the luminescent layers is not particularly limited. However, the total thickness is preferably set in the range from 2 nm to 5 μm, in view of homogenizing the layer thus formed, preventing a high voltage unnecessary at the light emission from being applied, and improving stability of a luminescent color against a driving current. More preferably, the total thickness is set in the range from 2 nm to 500 nm, most preferably in the range from 5 nm to 200 nm.

Further, in the present invention, a thickness of each luminescent layer is preferably set in the range from 2 nm to 1 μm, more preferably in the range from 2 nm to 200 nm, most preferably in the range from 3 nm to 150 nm.

The light luminescent layer used in the present invention preferably contains a luminescent dopant (or simply called a dopant) and a host compound (or called a luminescent host, simply called a host).

(1) Luminescent Dopant

As a luminescent dopant, preferably used are a phosphorescent dopant (or called a phosphorescent compound), and a fluorescent dopant (or called a fluorescent compound). In the present invention, preferably at least one of the luminescent layers contains a phosphorescent dopant.

A concentration of the luminescent dopant in the luminescent layer may be optionally determined based on required conditions of a specific dopant and device to be used. The luminescent dopant may be contained at a uniform concentration in a thickness direction of the luminescent layer. Further, the luminescent dopant may have optional concentration distribution.

Moreover, as the luminescent dopant used in the present invention, plurality kinds of luminescent dopants may be used together simultaneously. Alternatively, combination of the luminescent dopants having a different structure each other, or combination of a fluorescent dopant and a phosphorescent dopant may be used. This composition enables any luminescent color to be generated.

Figure 4:
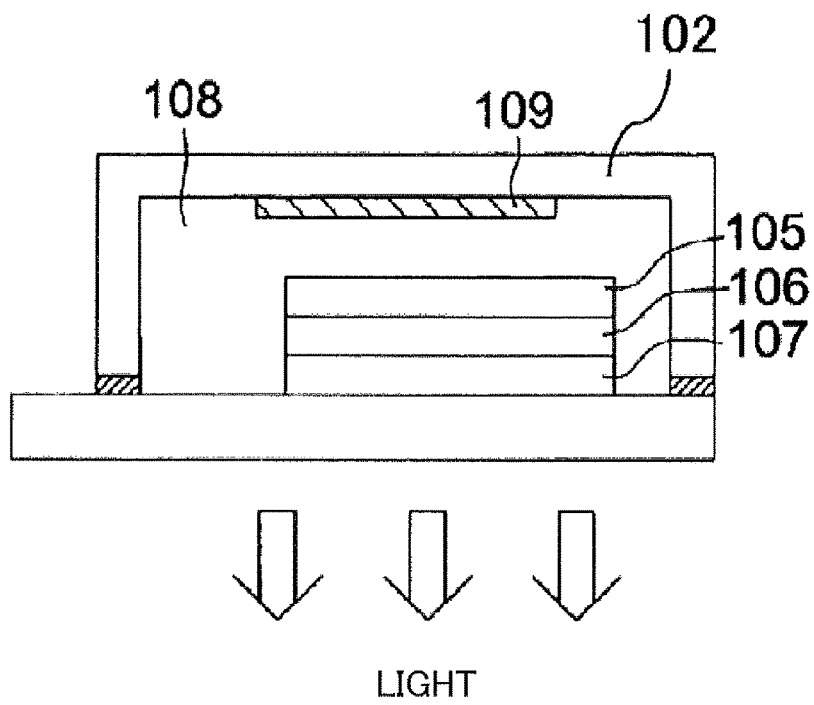
FIG. 4 is a perspective cross-sectional diagram schematically exemplifying a lighting device including an organic EL element of the present invention.

As for the organic EL element of the present invention, a color of light emitted by the compounds of the present invention is determined by a color obtained when measurement results collected by the spectral radiance meter CS-1000 (Konica Minolta Inc.) are adapted to the CIE chromaticity coordinate with referring to FIG. 4.16 in page 108 of "New Version of Color Science Handbook" (edited by the Color Sci. Association of Japan, The University of Tokyo Press, 1985).

In the present invention, preferably a single or a plurality of the luminescent layers may contain a plurality of the luminescent dopants having a different luminescent color each other, thereby achieving white light emitting.

Combination of the luminescent dopants showing a white color is not specifically limited. However, such combination includes, for example, combination of the luminescent dopants showing blue and orange colors, or combination of the luminescent dopants showing blue, green and red colors.

A white color with respect to the organic EL element of the present invention is not particularly limited, and may be a pale orange-containing white color or a pale blue-containing white color. However, preferably such a white color is set so that the chromaticity in the CIE1931 color system at 1000 cd/m$^2$ is in the range defined as: X=0.39±0.09, y=0.38±0.08, when the front-surface luminance of a 2° viewing angle is measured by the above described method.

(1.1) Phosphorescence Emission Dopant

A phosphorescence emission dopant (hereinafter, also referring to as a phosphorescent dopant) used in the present invention will be described more specifically.

A phosphorescent dopant used in the present invention is a compound of which luminescence generated from the exited triplet state is observed. Specifically, the phosphorescent dopant is a compound emitting phosphorescence at a room temperature (i.e., 25° C.), and defined as a compound of which phosphorescent quantum yield is 0.01 or more at 25° C. Preferably, the phosphorescent quantum yield is 0.1 or more.

The above phosphorescent quantum yield is measured by a method describes in "4th Edition Experimental Chemistry Course, Spectroscopy, vol. 7, p. 398, 1992, Maruzen, Ltd.). A phosphorescent quantum yield in a solution is measured by using various solvents. Herein, a phosphorescent dopant of the present invention should have the above described phosphorescent quantum yield (i.e., 0.01 or more) in any of optional solvents.

In principal, there are two types of luminescence of a phosphorescent dopant. One is an energy transfer type of luminescence generated by the process in which carries are recombined on a host compound which transfers the carries thereby to bring the host compound to an excited sate, and then the phosphorescent dopant emits luminescence via energy transfer from the exited state. The other is a carrier trap type of luminescence generated by the process in which the phosphorescent dopant acts as a carrier trap, and then carriers are recombined on the phosphorescent dopant thereby to emit luminescence by the phosphorescent dopant. In both types, energy of the exited state of the phosphorescent dopant has to be lower than that of the host compound.

A phosphorescent dopant used in the present invention may be appropriately selected from known phosphorescent dopants used in a luminescent layer of a conventional organic EL element.

More specific examples of known phosphorescent dopants usable in the present invention include the compounds described in the following documents.

Nature 395, 151 (1998); Appl. Phys. Lett. 78, 1622 (2001); Adv. Mater. 19, 739 (2007); Chem. Mater. 17, 3532 (2005); Adv. Mater. 17, 1059 (2005); WO2009/100991, WO2008/101842, WO2003/040257; US patent application publication Nos. 2006/835469, 2006/0202194, 2007/0087321, 2005/0244673; Inorg. Chem. 40, 1704 (2001); Chem. Mater. 16, 2480 (2004); Adv. Mater. 16, 2003 (2004); Angew. Chem. Int. Ed. 2006, 45, 7800; Appl. Phys. Lett. 86, 153505 (2005); Chem. Lett. 34, 592 (2005); Chem. Commun. 2906 (2005); Inorg. Chem. 42, 1248 (2003); WO2009/050290, WO2002/015645, WO2009/000637; US patent application publication No. 2002/0034656, U.S. Pat. No. 6,687,266, US patent application publication Nos. 2007/0190359, 2006/0008670, 2009/0165846, 2008/0015355;

U.S. Pat. Nos. 7,250,226, 7,396,598; US patent application publication Nos. 2006/0263635, 2003/0138657, 2003/0152802, U.S. Pat. No. 7,090,928; Angew. Chem. Int. Ed. 47, 1 (2008); Chem. Mater. 18, 5119 (2006); Inorg. Chem. 46, 4308 (2007); Organometallics 23, 3745 (2004); Appl. Phys. Lett. 74, 1361 (1999); WO2002/002714, WO2006/009024, WO2006/123873, WO2005/123873, WO2007/040380, WO2006/082742; US patent application publication Nos. 2006/0251923, 2005/0260441; U.S. Pat. Nos. 7,393,599, 7,534,505, 7,445,855; US patent application publication Nos. 2007/0190359, 2008/0297033; U.S. Pat. No. 7,338,722, US patent application publication No. 2002/0134984, U.S. Pat. No. 7,279,704; US patent application publication Nos. 2006/098120, 2006/103874; WO2005/076380, WO2010/032663, WO2008/140115, WO2007/052431, WO2011/134013, WO2011/157339, WO2010/086089, WO2009/113646, WO2012/020327, WO2011/051404, WO2011/004639, WO2011/073149; US patent application publication Nos. 2012/228583, 2012/212126; Japanese unexamined patent application publication Nos. 2012-069737, 2012-195554, 2009-114086, 2003-81988, 2002-302671 and 2002-363552.

Among the above compounds, a preferable phosphorescent dopant is an organometallic complex having Ir as a center metal. More preferably, such a phosphorescent dopant is an organometallic complex including at least one of coordination styles selected from metal-carbon bond, metal-nitrogen bond, metal-oxygen bond, and metal-sulfur bond.

(1.2) Fluorescence Emission Dopant

A fluorescence emission dopant (hereinafter, also referring to as a fluorescent dopant) used in the present invention will be described more specifically.

The fluorescent dopant used in the present invention is a compound emitting light from an exited singlet state, but is not specifically limited so long as the luminescence generated from the exited singlet is observed.

The fluorescent dopant used in the present invention includes, for example, an anthracene derivative, a pyrene derivative, chrysene derivative, a fluoranthene derivative, a perylene derivative, a fluorene derivative, an arylacetylene derivative, a styrylarylene derivative, a styrylamine derivative, an arylamine derivative, a boron complex, a coumarin derivative, a pyrane derivative, a cyanine derivative, a croconium derivative, a squarylium derivative, an oxobenzanthrecene derivative, a fluoroscein derivative, a rhodamine derivative, a pyrylium derivative, a perylene derivative, a polythiophene derivative, or a rare earth complex base compound.

Further, recently a luminescent dopant using delayed fluorescence has been developed. Such a luminescent dopant may be used.

Specific examples of the luminescent dopant using delayed fluorescence include compounds disclosed in WO201/156793, Japanese unexamined patent application publication Nos. 2011-213643, 2010-93181. However, the present invention is not limited to those compounds.

(2) Host Compound

A host compound used in the present invention is a compound which performs injection and transfer of charges in the luminescent layer. In the organic EL element, the luminescence of the compound itself is not substantially observed.

Preferably, such a compound has a phosphorescent quantum yield of the phosphorescence at a room temperature (25° C.) in the range less than 0.1, more preferably less than 0.01. Further, the mass ratio of the compound in the luminescent layer against all of the compounds contained in the luminescent layer is preferably 20 mass % or more.

Moreover, preferably, excited state energy of the host compound is higher than that of the luminescent dopant contained in the same layer.

The host compound may be used alone or used with plurality kinds of host compounds. When plurality kinds of host compounds are used, the charge transfer may be controlled, allowing the luminescence of the organic EL element to be made highly efficient.

A host compound used in the present invention is not particularly limited, and therefore, compounds used in conventional organic EL elements may be used. Such a host compound may be a small compound or a polymer compound formed of repeated units. Further, the host compound may be compounds having a reactive group like a vinyl group and an epoxy group.

Preferably, known host compounds have functions for transferring holes and electrons, and simultaneously prevent elongation of a wave length of luminescence. Further, in view of stably driving the organic EL element against heat generated when driven at a high temperature or during the drive thereof, the host compound preferably has a high glass transfer temperature (Tg). Preferably, Tg is 90° C. or more, more preferably 120° C. or more.

Here, a glass transition temperature (Tg) is a value (or temperature) obtained by a method based on JIS-7121, using DSC (Differential Scanning Colorimetry).

Specific examples of known host compounds used in the organic EL element of the present invention include the compounds disclosed in the following documents. However, the present invention is not limited to those compounds.

Japanese unexamined patent application publication Nos. 2001-257076, 2002308855, 2001-313179, 2002-319491, 2001-357977, 2002-334786, 2002-8860, 2002-334787, 2002-15871, 2002-334788, 2002-43056, 2002-334789, 2002-75645, 2002-338579, 3002-105445, 2002-343568, 2002-141173, 2002-363227, 2002-231453, 2003-3165, 2002-234888, 2003-27048, 2002-255934, 2002-260861, 2002-280183, 2002-099060, 2002-302516, 2002-308837; US patent application publication Nos. 2003/0175553, 2006/0280965, 2005/0112407, 2009/0017330, 2009/0030202, 2005/0238919; WO2001/039234, WO2009/021126, WO2008/056746, WO2004/093207, WO2005/089025, WO2007/063796, WO2007/063754, WO2004/107822, WO2005/030900, WO2006/114966, WO2009/086028, WO2009/003898, WO2012/023947; Japanese unexamined patent application publication Nos. 2008-074939, 2007-254297; and European Patent No. 2034538.

<<Electron Transfer Layer>>

An electron transfer layer used in the present invention is made of materials having a function for transferring electrons. Specifically, the electron transfer layer should have a function for transferring electrons injected from the cathode to the luminescent layer.

A total thickness of the electron transfer layer used in the present invention is not particularly limited. However, typically the total thickness thereof is in the range from 2 nm to 5 μm, preferably 2 nm to 500 nm, more preferably 5 nm to 200 nm.

Further, it is known that when luminescence emitted from a luminescent layer is directly extracted from an electrode in an organic EL element, luminescence directly extracted from the luminescent layer causes interference with other luminescence to be extracted after having been reflected by another electrode oppositely positioned across the luminescent layer against the electrode from which the luminescence is directed extracted. When luminescence is reflected by a cathode, the above reflection phenomenon may be efficiently used by appropriately adjusting a total thickness of an electron transfer layer in the range from 5 nm to 1 µm.

On the other hand, increase in a total thickness of the electron transfer layer tends to raise a voltage. Therefore, when the total thickness is large, preferably electron mobility in the electron transfer layer is set at $10^{-5}$ cm$^2$/Vs or more.

A material used for the electron transfer layer (hereinafter, called an electron transfer material) should have one among an injection performance, a transfer performance or a barrier performance, and may be optionally selected from conventionally known compounds.

For example, such a material includes nitrogen-containing aromatic heterocyclic derivatives (e.g., a carbazole derivative, an azacarbazole derivative (i.e., a derivative in which at least one carbon atom of a carbazole ring is replaced with a nitrogen atom)), a pyridine derivative, a pyrimidine derivative, a pyrazine derivative, a pyridazine derivative, a triazine derivative, a quindoline derivative, a quinoxaline derivative, a phenanthroline derivative, an azatriphenylene derivative, an oxazole derivative, a triazole derivative, an oxadiazole derivative, a thiadiazole derivative, a triazole derivative, a benzimidazole derivative, a benzoxazole derivative, a benzothiazole derivative, a dibenzofuran derivative, a dibenzothiophene derivative, a silole derivative, and aromatic hydrocarbon derivatives (e.g., a naphthalene derivative, an anthracene derivative, a triphenylene derivative).

Further, the following metal complexes may be used for the electron transfer material.

A metal complex having a quinolinol skeleton and a dibenzoquinolinol skeleton in ligands may be used for the electron transfer material. For example, such metal complexes include tris(8-quinolinol) aluminum (Alq), tris(5,7-dichloro-8-quinolinol) aluminum, tris(5,7-dibromo-8-quinolinol) aluminum, tris(2-methyl-8-quinolinol) aluminum, tris(5-methyl-8-quinolinol) aluminum, bis(8-quinolinol)Zn (Znq) or the like, and a metal complex derived from the above described metal complexes of which center metal is replaced with Ir, Mg, Cu, Sn. Ga, or Pb.

In addition, metal free phthalocyanine or metal phthalocyanine, and metal free or metal phthalocyanine derivatives in which the terminal group is substituted with an alkyl group or a sulfonate group may be preferably used as the electron transfer material. Further, distyrylpyrazine derivatives exemplified as the luminescent layer material may be used for the electron transfer material. Moreover, inorganic semiconductors such as n-type Si and n-type SiC similarly to the hole injection layer and hole transfer layer may be used for the electron transfer material.

Furthermore, a polymer material prepared by introducing the above described materials into the polymer chain, or a polymer material having those materials as the main chain may be also used for the electron transfer material.

The electron transfer layer used in the present invention may be formed by doping a dope material thereon as a guest material, thereby to form a high n-type (or electron rich) layer. The dope material includes an n-type dopant made of a metal compound such as a metal complex or a metal halide. Specific examples of the electron transfer layer having the above compositions are disclosed by the following documents: Japanese unexamined patent application publication Nos. Hei4-297076, Hei10-270172, 2000-196140, 2001-102175, and J. Appl. Phys. 95, 5773 (2004).

Specific examples of the known and preferable electric transfer material used in the organic EL element of the present invention include the compounds described in the following documents. However, the present invention is not limited to those compounds.

U.S. Pat. Nos. 6,528,187, 7,230,107; US patent application publication Nos. 2005/0025993, 2004/0036077, 2009/0115316, 2009/0101870, 2009/0179544; WO2003/060956, WO2008/132085; Appl. Phys. Lett. 75, 4 (1999); Appl. Phys. Lett. 79, 449 (2001); Appl. Phys. Lett. 81, 162 (2002); Appl. Phys. Lett. 79, 156 (2001); U.S. Pat. No. 7,964,293; US patent application publication No. 2009/030202; WO2004/080975, WO2004/063159, WO2005/085387, WO2006/067931, WO2007/086552, WO2008/114690, WO2009/069442, WO2009/066779, WO2009/054253, WO2011/086935, WO2010/150593, WO2010/047707; European Patent No. 2311826; Japanese patent application publication Nos. 2010-251675, 2009-209133, 2009-124114, 2008-277810, 2006/156445, 2005-340122, 2003-45662, 2003-31367, 2003-282270; and WO2012/115034.

More preferable electron transfer materials of the present invention include a pyridine derivative, a pyrimidine derivative, a pyrazine derivative, a triazine derivative, a dibenzofuran derivative, a dibenzothiophene derivative, a carbazole derivative, an azacarbazole derivative, and a benzimidazole derivative.

The electron transfer material may be used alone or in combination with the plurality of materials.

<<Hole Blocking Layer>>

A hole blocking layer is a layer having a function of an electron transfer layer in a broad sense. Preferably, the hole blocking layer is made of a material having an ability of transferring holes but simultaneously having a little ability of transferring electrons. The ability of transferring electrons but simultaneously preventing transference of holes enables improvement in recoupling probability of electrons and holes.

Further, the above described structures of the electron transfer layer may be used as a hole blocking layer of the present invention, as needed.

The hole blocking layer arranged in the organic EL element of the present invention is preferably disposed adjacent to a cathode side of the luminescent layer.

A thickness of the hole blocking layer used in the present invention is preferably in the range from 3 nm to 100 nm, more preferably from 5 nm to 30 nm.

A material used for the hole blocking layer is preferably a material used for the above described electron transfer layer, and also a material used for the above described host compound.

<<Electron Injection Layer>>

An electron injection layer used in the present invention (or called a "cathode buffer layer") is a layer provided between the cathode and the luminescent layer for decreasing the driving voltage and improving the luminescent brightness. The above feature is described in detail in "Organic EL Element and Frontiers of the Industrialization", 2nd Ed., Chapter 2, "Electrode Material" (pp. 123-166), published by NTS Inc., Nov. 30, 1998.

In the present invention, the electron injection layer may be provided as needed, and located between the cathode and the luminescent layer as mentioned above, or between the cathode and the electron injection layer.

Preferably, the electron injection layer is an extremely thin film, and the thickness is in the range from 0.1 nm to 5 nm depending on the raw material. Alternatively, the electron injection layer may be a heterogeneous film in which composition materials intermittently exist.

The electron injection layer is described in detail in Japanese patent application publication Nos. Hei06-325871, Hei09-17574, Hei10-74586. Examples of the materials preferably used for the electron injection layer include a metal such as strontium and aluminum; an alkaline metal compound such as lithium fluoride, sodium fluoride, potassium fluoride; an alkaline earth metal compound such as magnesium fluoride, calcium fluoride; a metal oxide such as aluminum oxide; a metal complex such as lithium 8-hydroxyquinolate (Liq). Alternatively, the electron transfer materials described above may be also used for the electron injection layer.

Herein, the above materials used for the electron injection layer may be used alone or in combination with the plurality kinds of materials.

<<Hole Transfer Layer>>

A hole transfer layer used in the present invention is made of a material having a function for transferring holes, and should have a function for conducting holes thus injected from the anode to the luminescent layer.

A total thickness of the hole transfer layer used in the present invention is not specifically limited. However, typically, the total thickness is in the range from 5 nm to 5 μm, preferably from 2 nm to 500 nm, more preferably from 5 nm to 200 nm.

A material used for the hole transfer layer (hereinafter, called a hole transfer material) should have one property among an injection property of holes, a transfer property of holes, or a barrier property of electrons. Therefore, optional materials selected from conventionally known compounds may be used for the hole transfer layer of the present invention.

For example, such materials include a porphyrin derivative, a phthalocyanine derivative, an oxazole derivative, an oxadiazole derivative, a triazole derivative, an imidazole derivative, a pyrazoline derivative, a pyrazoline derivative, a phenylenediamine derivative, a hydrazone derivative, a stilbene derivative, a polyaryl alkane derivative, a triarylamine derivative, a carbazole derivative, an indolocarbazole derivative; an acene derivative such as anthracene and naphthalene; a fluorene derivative, a fluorenone derivative, a polymer material or oligomer introduced with polyvinylcarbazole or an aromatic amine into the main chain of aside chain thereof; polysilane; a conductive polymer of oligomer (e.g., PEDOT: PSS, aniline base copolymer, polyaniline, polythiophene) or the like.

A triarylamine derivative includes a benzidine type compound such as α-NPD, a star-burst type compound such as MTDATA, and a compound having a fluorene or anthracene part at a triarylamine linkage core or the like.

Further, a hexaazatriphenylene derivative described in Japanese unexamined patent application publication Nos. 2003-519432 and 2006-135145 may be used for the hole transfer material.

Moreover, a hole transfer layer having a high p-property doped with an impurity may be also used. Such examples are described in Japanese unexamined patent application publication Nos. Hei04-297076, 2000-196140, 2001-102175, and J. Appl. Phys. 95, 5773 (2004).

Furthermore, an inorganic compound such as a so-called p-type hole transfer material and p-type-Si, p-type-SiC may be also used. Additionally, an ortho-metalated organometallic complex having Ir or Pt as a center metal such as Ir(ppy)$_3$ may be preferably used.

The above described materials may be used for the hole transfer material. Herein, preferably a triarylamine derivative, a carbazole derivative, an indolocarbazole derivative, an azatriphenylene derivative, an organometallic complex, a polymer material or oligomer introduced with an aromatic amine in the main chain or a side chain.

Examples of known and preferable hole transfer materials used for the organic EL element of the present invention include the compounds described in the following documents besides the above listed documents. However, the present invention is not limited to those For example, listed are Appl. Phys. Lett. 69, 2160 (1996); J. Lumin. 72-74, 985 (1997); Appl. Phys. Lett. 90, 183 (2007); Appl. Phys. Lett. 90, 503 (2007); Appl. Phys. Lett. 51, 913 (1987); Synth. Met. 87, 171 (1997); Synth. Met. 91, 209 (1997); Synth. Met. 111, 421 (2000); SID Symposium Digest 37, 923 (2006); J. Mater. Chem. 3, 319 (1993); Adv. Mater. 6, 677 (1994); Chem. Mater. 15, 3148 (2003); US Patent application publication Nos. 2003/0162053, 2002/0158242, 2006/0240279, 2008/0220265; U.S. Pat. No. 5,061,569; WO2007/002683, WO2009/018009, European patent No. 650955; US Patent application publication Nos. 2008/0124572, 2007/0278938, 2008/0106190, 2008/0018221; WO2012/115034; Japanese unexamined patent application publication Nos. 2003-519432, 2006-135145; and U.S. patent application Ser. No. 13/585,981.

Here, the hole transfer materials may be used alone or in combination with the plurality kinds of materials.

<<Electron Blocking Layer>>

In a broad sense, an electron blocking layer is a layer having a function of a hole transfer layer, preferably made of a material having a function for transferring holes as well as a little ability for transferring electrons. The ability of transferring holes and simultaneously blocking electrons enables improvement in the recoupling probability of electrons and holes.

Further, the above described structures of the hole transfer layer may be used for the electron blocking layer used in the present invention as needed.

Preferably, an electron blocking layer provided in the organic EL element of the present invention may be arranged adjacent to an anode side of the luminescent layer.

A thickness of the electron blocking layer used in the present invention is preferably in the range from 3 nm to 100 nm, more preferably from 5 nm to 30 nm.

A material used for the electron blocking layer is preferably a material used for the above mentioned materials used for the hole transfer layer. Further, the materials used for the above mentioned host compounds are also preferably used for the electron blocking layer.

<<Hole Injection Layer>>

A hole injection layer used in the present invention (or called an "anode buffer layer") is a layer provided between the anode and the luminescent layer for lowering the driving voltage and improving the luminescent brightness. The above feature is described in detail in "Organic EL Element and Frontiers of the Industrialization", $2^{nd}$ Ed., Chapter 2, "Electrode Material" (pp. 123-166), published by NTS Inc., Nov. 30, 1998.

In the present invention, the hole injection layer may be provided as needed, and placed between the anode and the luminescent layer as mentioned above, or between the anode and the hole transfer layer.

The hole injection layer is described in detail in Japanese patent application publication Nos. Hei09-45479, Hei09-260062, Hei08-288069 or the like. Materials used for the hole injection layer include, for example, the above described materials used for the hole transfer layer.

Among the materials, especially preferable are a phthalocyanine derivative such as copper phthalocyanine; a hexaazatriphenylene derivative described in Japanese unexamined patent application publication Nos. 2003-519432, 2006-135145; a metal oxide such as vanadium oxide; amorphous carbon; a conductive polymer such as emeraldine base polyaniline and polythiophene; an ortho-metalated complex such as tris(2-phynylpyridine) iridium complex; and a triarylamine derivative.

Here, the above described hole injection materials may be used alone or in combination with the plurality kinds of materials.

<<Inclusion>>

An organic layer of the present invention may further include another compound.

Such an inclusion is, for example, a halogen element such as bromine, iodine and chlorine; a halogenated compound such as a bromide, an iodide and a chloride; alkaline and alkaline earth metals such as Pd, Ca, Na; a transition metal compound; a complex or a salt of a transition metal compound or the like.

An amount of the inclusion may be optionally determined. Herein, preferably, the content of the inclusion against a total mass of the layer having the inclusion is 1000 ppm or less, more preferably 500 ppm or less, and most preferably 50 ppm or less.

Note, the present invention is not limited to the above mentioned values of the content. The content of the inclusion may not fall in the above range depending on a purpose for improving the transferring performance of electrons and holes, and a purpose for facilitating the energy transfer of excitons.

<<Method for Forming Organic Layers>>

Next, a method for forming organic layers used in the present invention (e.g., a hole injection layer, a hole transfer layer, an electron blocking layer, a luminescent layer, a hole blocking layer, an electron transfer layer, and an electron injection layer) will be described in detail.

A method for forming organic layers used in the present invention is not particularly limited. For example, a conventionally known method may be used including a vacuum deposition, a wet process or the like. Herein, preferably the organic layer is formed by a wet process. That is, the organic EL element is preferably prepared by a wet process. Such a wet process applied to a preparation of the organic EL element exerts the advantageous effects so that a homogeneous film (or a coating film) is easily obtained, and simultaneously a pin-hole is hardly generated. Note, the film (or the coating film) described herewith is in a state having been dried after coated by the wet process.

The wet process includes spin coating, ink jet, printing, die coating, blade coating, roll coating, spray coating, a curtain coating, an LB method (Langmuir-Blodgett technique). Herein, in view of easy preparation of a homogeneous thin film as well as high producibility, a method more suitable for a roll-to-roll method is preferable, including die-coating, roll coating, ink jet, spray coating or the like.

A liquid medium dissolving or dispersing the organic EL material of the present invention is an organic solvent, for example, including ketones such as methyl ethyl ketone, cyclohexanone; aliphatic acid esters such as ethyl acetate; halogenated hydrocarbons such as dichlorobenzene; aromatic hydrocarbons such as toluene, xylene, mesitylene, cyclohexylbenzene; aliphatic hydrocarbons such as cyclohexane, decalin, dodecane; N,N-dimethylformamide (DMF) and dimethylsulfoxide (DMSO) or the like.

Here, a dispersion method includes, for example, ultrasonic dispersing, high-shear dispersing, or media dispersing or the like.

Further, a different coating method may be applied to each layer. When a vapor deposition method is used for the film coating, conditions of the vapor deposition method vary depending on the types of compounds used therein. Generally, the conditions are suitably selected from the following ranges, for example, a boat heating temperature in the range from 50° C. to 450° C.; a degree of vacuum in the range from $10^{-6}$ Pa to $10^{-2}$ Pa; a vapor deposition rate in the range from 0.01 nm/sec to 50 nm/sec; a substrate temperature in the range from −50° C. to 300° C.; a thickness in the range from 0.1 nm to 5 µm, preferably from 5 nm to 200 nm.

The organic layers used in the present invention are preferably formed in a single vacuuming operation and consistently prepared from the hole injection layer to the cathode. However, during the film coating procedure, a half-coated product may be taken out, and subsequently subjected to a different film coating method. At that time, preferably the film coating may be performed under a dry and inert gas atmosphere.

<<Anode>>

An anode made of an electrode material including a metal, an alloy, an electric conductive compound or a mixture thereof all of which have a large work function (e.g., 4 eV or more, preferably 4.5 eV more) may be preferably used for an anode in the organic EL element. Examples of such an electrode material are a metal such as Au, conductive transparent material such as CuI, indium tin oxide (ITO), $SnO_2$, ZnO. Further, a material capable of preparing an amorphous and transparent conductive film such as IDIXO ($In_2O3-ZnO$) may be used.

The anode may be prepared by forming a thin film via vapor depositing or spattering those electrode materials, and forming a pattern having a desirable shape via a photolithography method. Alternatively, when high accuracy of patterning is not needed (i.e., about 100 µm or more), a pattern may be formed through a mask having a desirable shape while subjected to vapor depositing or spattering of the above described electrode materials.

Further, when a material capable of being applied such as an organic conductive compound is used, a wet film coating method such as a printing method and a coating method may be used. Further, when luminescence is extracted from the above described anode, preferably transparency thereof is set at larger than 10%, and sheet resistance thereof is set in several hundreds Ω/□ or less.

A thickness of the anode depends on a material. However, typically the thickness is selected in the range from 10 nm to 1 µm, preferably from 10 nm to 200 nm.

<<Cathode>>

A cathode made of an electrode material including a metal (or called a metal having an electron injection property), an alloy, an electric conductive compound or a mixture thereof all of which have a small work function (e.g., 4 eV or less) may be preferably used. Examples of such an electrode material are a metal such as sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, aluminum, and a rear earth metal or the like.

Among the above materials, in view of the electron injection property and the durability against oxidation, preferable materials are a mixture of a metal having an electron injection property and a secondary metal being stable and having a larger value of the work function than said metal, for example, including a magnesium/silver mixture, magnesium/aluminum mixture, a magnesium/indium mixture, an aluminum/aluminum oxide ($Al_2O_3$) mixture, a lithium/aluminum mixture, and aluminum or the like.

The cathode may be prepared by forming a thin film by vapor depositing or spattering the above described electrode materials. Further, preferably sheet resistance of the cathode is set in several hundreds Ω/□ or less, and a thickness thereof is typically selected in the range from 10 nm to 5 μm, preferably from 50 nm to 200 nm.

Herein, when either of the cathode and the anode in the organic EL element is transparent or semitransparent, this configuration enables improvement in the luminescent brightness and convenience.

Further, a transparent or semitransparent cathode may be prepared by forming the above metal with a thickness from 1 nm to 20 nm and subsequently forming a conductive transparent material exemplified in the descriptions of the anode. When the transparent or semitransparent cathode is used, the element including both transparent cathode and anode may be prepared.

<Support Substrate>>

As for a support substrate (hereinafter, also called a base body, a substrate, a base material, a support) used for the organic EL element of the present invention, types of glass and plastics are not specifically limited, and the support substance may be transparent or opaque. When luminescence is extracted from a side of a support substrate, preferably the support substrate is transparent. A transparent support substrate preferably used in the present invention includes, glass, quart, a transparent resin film. A most preferable support substrate is a resin film capable of affording flexibility to the organic EL element.

Such a resin film includes, for example, polyesters such as polyethylene terephthalate (PET), polyethylene naphthalate (PEN); cellulose esters or derivatives thereof such as polyethylene, polypropylene, cellophane, cellulose diacetate, cellulose triacetate (TAG), cellulose acetate butyrate, cellulose acetate propionate, (CAP), cellulose acetate phthalate, cellulose nitrate; poly vinylidene chloride, polyvinyl alcohol, polyethylene vinyl alcohol, syndiotactic polystyrene, polycarbonate, norbornene resin, polymethylpentene, polyether ketone, polyimide, polyethersulfone (PES), polyphenylene sulfide, polysulfones, polyetherimide, polyether ketene imide, polyamide, fluororesin, nylon, polymethyl methacrylate, acryl or polyarylate, cycloolefin base resin such as Alton (registered, JSR Co.) or Abel (registered, Mitsui Chemicals, Inc.).

On a surface of the resin film, an inorganic or organic coating film, or a hybrid coating film thereof may be formed. Such a film is preferably a barrier film having 0.01 or less g/($m^2$·24 h) of water vapor permeability (i.e., at 25±0.5° C. and relative humidity (90±2)% RH) measured following JIS K 7129-1992, and more preferably a high barrier film having $10^{-3}$ or less ml/($m^2$·24 h·atm) of oxygen permeability measured following JIS K 7126-1987 and $10^{-5}$ g/($m^2$·24 h) of water vapor permeability.

A material forming the barrier film should have a function for suppressing penetration of substances such as water and oxygen deteriorating the substrate, for example, including silicon oxide, silicon dioxide, silicon nitride. Further, the barrier film is preferably has a stacking structure comprised of those organic layers and inorganic layers in order to improve the fragility of the film. Herein, the stacking order of the organic layers and the inorganic layers is not particularly limited. However, preferably the organic layer and the inorganic layer are alternately stacked one another multiple times.

A method for forming the barrier film is not particularly limited. For example, various methods may be applicable including a vacuum vapor deposition method, a spattering method, a reactive spattering method, a molecular beam epitaxy method, a cluster-ion beam method, an ion plating method, a plasma polymerization method, an atmospheric plasma polymerization method, a plasma CVD method, a laser CVD method, a thermal CVD method, a coating method or the like. Herein, the most preferable one is an atmospheric plasma polymerization method disclosed in Japanese unexamined patent application publication No. 2004-68143.

An opaque support substrate includes, for example, a metal plate made of aluminum or stainless steel, a film or opaque resin substrate, or a ceramic substrate.

External extraction quantum efficiency of the organic EL element of the present invention at a room temperature is preferably 1% or more, more preferably 5% or more.

Here, the external extraction quantum efficiency is represented by the following equation.

[External Extraction Quantum Efficiency (%)]= [Number of Photons Emitted to Outside of Organic EL Element]/[Number of Electrons Flowing in Organic EL Element]×100

Further, a hue improvement filter such as a color filter may be used together, or a color conversion filter converting the luminescent color emitted from the organic EL element to multiple colors via a fluorescent substance may be used together.

<<Sealing>>

A method for sealing the organic EL element of the present invention includes, for example, a method for bonding a sealing member, the electrodes, and the support substrate together via an adhesive. A sealing member may have a concave shape or a flat shape as long as the member is arranged to cover a display region of the organic EL element. Further, the transparence or the electric insulation thereof is not specifically limited.

Examples of the sealing member include a glass plate, a polymer plate and a metal plate or the like. Such a glass plate specifically includes barium-strontium containing glass, lead glass, alminosilicate glass, borosilicate glass, barium borosilicate glass, and quartz. Further, examples of the polymer plate include polycarbonate, acryl, polyethylene terephthalate, polyether sulfide, and polysulphone or the like. Examples of the metal plate may be at least one kind of metals or alloys selected from stainless steel, iron, copper, aluminum, magnesium, nickel, zinc, chromium, titanium, molybdenum, silicon, germanium, and tantalum.

In the present invention, a polymer film and a metal film may be preferably used due to the capability of making the organic EL element thinner. Further, the polymer film is preferably has $1\times10^{-3}$ or less ml/($m^2$·24 h·atm) of the oxygen permeability measured following a method of JIS K 7126-1987, and $1\times10^{-3}$ or less g ($m^2$·24 h) of the water vapor permeability (at 25±0.5° C., relative humidity of 90±2%) measured with following a method of JIS K 7129-1992.

The sealing member is fabricated to have a convex shape by sandblast fabrication and chemical etching fabrication or the like.

Examples of the adhesive include a photocuring or thermosetting type adhesive having a reactive vinyl group of an acrylic acid oligomer or a methacryl acid oligomer; a moisture curing type adhesive such as 2-cyanoacrylic acid ester or the like; and a thermal setting and photocuring type adhesive (i.e., two liquid mixing type) such as an epoxy base one. Further, the examples include a hot melt type of polyamide, polyester and poly olefin, and a cation curing type of ultraviolet curing type epoxy resin adhesive.

Herein, preferably the adhesive has bonding and curing functions at the temperature from a room temperature to 80° C. since the organic EL element may be deteriorated by a thermal treatment. Further, a desiccant may be dispersed in the adhesive. A commercially available dispenser may be used for applying the adhesive to the sealing member, or the application be performed by printing like screen printing.

Alternatively, preferably the sealing film may be formed by covering external sides of the electrode and the organic layer positioned opposite to the support substrate across the organic layer, and forming an inorganic or an organic layer so as to be adjacent to the support substrate. In this case, a material of forming the film should have a function for preventing permeation of substances which deteriorate the element such as water and oxygen. For example, silicon oxide, silicon dioxide, silicon nitride or the like may be used.

Further, the sealing film preferably has a stacking structure comprised of the organic layers and inorganic layers in order to improve the fragility of the film. Herein, a method for forming the sealing film is not particularly limited. For example, various methods may be applicable including a vacuum vapor deposition method, a spattering method, a reactive spattering method, a molecular beam epitaxy method, a cluster-ion beam method, an ion plating method, a plasma polymerization method, an atmospheric plasma polymerization method, a plasma CVD method, a laser CVD method, a thermal CVD method, a coating method or the like.

Preferably, an inert gas such as nitrogen or argon in case of a gas phase, or an inert liquid such as a fluorohydrocarbon or a silicon oil in case of a liquid phase may be injected into a gap between the sealing member and the display region of the organic EL element. Alternatively, such a gap may be vacuumed, or a desiccant may be sealed inside the gap.

Such a desiccant includes, for example, a metal oxide (e.g., sodium oxide, potassium oxide, calcium oxide, barium oxide, magnesium oxide, aluminum oxide), a sulfonate (e.g., sodium sulfonate, calcium sulfonate, magnesium sulfonate, cobalt sulfonate), a metal halide (e.g., calcium chloride, magnesium chloride, cesium fluoride, tantalum fluoride, cerium bromide, magnesium bromide, barium iodide, magnesium iodide), a perchlorate (e.g., barium perchlorate, magnesium perchlorate). Herein, an anhydrous salt is preferably used in case of sulfates, metal halides and perchlorates.

<<Protection Film, Protection Plate>>

A protection film or a protection plate may be provided at an external side of the sealing film or the film for sealing placed at the opposite side to the support substrate across the organic layer, in order to increase the mechanical strength of the element. Specifically, when the sealing is performed by the above described sealing film, such a protection film or protection plate is preferably provided because mechanical strength of the element is not necessarily high. A material used for the protection film and plate may preferably include a glass plate, a polymer plate and a metal plate the same as used for the above described sealing. However, in view of light in weight and thin in film thickness, preferably a polymer film is used.

<<Technology for Improving Luminescence Extraction>>

It is generally said that an organic electroluminescent element emits luminescence inside a layer having a larger relative index (i.e., relative index in the range from about 1.6 to about 2.1) than air, and only about 15% to 20% of the luminescence generated at the luminescent layer can be extracted.

This is because luminescence incident on an interface (i.e., an interface between a transparent substrate and air) at an incident angle of θ equal to and more than a critical angle totally reflects, making it hard to extract the luminescence outside the element. Further, such luminescence totally reflects between a transparent layer and a transparent electrode or a luminescent layer, thereby to be waveguided through the transparent electrode or the luminescent layer. Accordingly, the luminescence is released in a direction to a side of the element.

A method for improving the efficiency of the luminescence extraction includes, for example, a method for preventing total reflection on an interface between a transparent substrate and air by forming concaves and convexes on a surface of the transparent substrate (e.g., U.S. Pat. No. 4,774,435); a method for improving the efficiency by making a substrate light-condensing (e.g., Japanese unexamined patent application publication No. Sho63-314795; a method for forming a reflection surface on an element side (e.g., Japanese unexamined patent application publication No. Hei01-220394); a method for forming a reflection preventing film by introducing a flat layer having a middle range of refractive index between a substrate and a luminescent body (e.g., Japanese unexamined patent application publication No. Sho62-172691); a method for introducing a flat layer having a refractive index lower than a substrate between a substrate and a luminescent body (e.g., Japanese unexamined patent application publication No. 2001-202827); and a method for forming a diffraction grating between a pair of layers comprised of a substrate, a transparent electrode layer and a luminescent layer (further including: between a substrate and the outside) (e.g., Japanese unexamined patent application publication No. Hei11-283751).

In the present invention, the above methods may be used combining with the organic EL element of the present invention. Herein, among the methods, the following ones are preferably used including a method for introducing a flat layer having a refractive index lower than a substrate between a substrate and a luminescent body or a method for forming a diffraction grating between a pair of layers comprised of a substrate, a transparent electrode layer and a luminescent layer (further including: between a substrate and the outside).

In the present invention, combination of the above methods enables the element more excellent in high brightness or durability to be provided.

When a medium having a low refractive index is formed between the transparent electrode and the transparent substrate with a thickness longer than a wavelength of the luminescence, the extraction efficiency of the luminescence emitted from the transparent electrode to the outside becomes higher as the refractive index of the medium becomes lower.

Such a layer with a low refractive index includes, for example, aerogel, porous silica, magnesium fluoride, fluorine polymer or the like. A refractive index of the transparent substrate is generally in the range from about 1.5 to about 1.7. Thus, preferably a layer with a low refractive index has a refractive index of 1.5 or less, more preferably 1.35 or less.

A thickness of the medium with a low refractive index is desirably set to 2-fold or more of a wavelength of light in the medium. This is because the effect of the layer with a low refractive index is decreased when the thickness of the medium with a low refractive index becomes around a wavelength of light and eventually to a thickness at which an electromagnetic wave running out as an evanescent wave enters the substrate.

A method for introducing a diffraction grating into an interface which causes total reflection or any one of the media has an advantage to highly improve the efficiency for extracting light. Such a method uses property of a diffraction grating capable of changing a direction of light to a specific one different from the refraction direction of light by so-called Bragg diffraction like primary diffraction, secondary diffraction.

Namely, the method is performed via introducing a diffraction grating between any of two layers adjacent each other or in any medium (i.e., inside a transparent substrate or a transparent electrode), diffracting light incapable of going outside because of total reflection between a pair of layers among the light generated from a luminescent layer, and eventually extracting said light therefrom.

Preferably, the diffraction grating to be introduced has a two-dimensional periodical refractive index. Here, light emitted from the luminescent layer randomly generates in all directions. A typical one-dimensional diffraction grating having periodical refractive index distribution in all directions can diffract only the light travelling in a specific direction. This makes it difficult to significantly improve the efficiency for extracting light.

On the contrary, when the refractive index distribution is made to be two-dimensional distribution, light traveling in all directions is diffracted, resulting in improvement of the efficiency for extracting light.

A position at which a diffractive grating is introduced may be between any of two layers adjacent each other, or in any medium (i.e., inside a transparent substrate or a transparent electrode), but desirably at a vicinity of the organic luminescent layer at which light emits. In this case, a period of the diffraction grating is preferably set in the range from about ½ to about 3-fold length of a wavelength of light in the medium. Preferably, an arrangement of the diffraction grating is two-dimensionally repeated such as a square lattice-like, a triangle lattice-like, and a honeycomb lattice-like.

<<Light Condensing Sheet>>

The organic EL element of the present invention may be fabricated so that a microlens array-like structure is provided at a light extracting side of the support substrate (or substrate), or combined with a so-called light condensing sheet. This configuration enables improvement of the brightness in the specific direction by condensing light in the specific direction, for example, in the front direction against a luminescent surface of the element.

As examples of a microlens array, quadrangular pyramids are two-dimensionally arranged at a light extracting side of the substrate, each quadrangular pyramid having a side length of 30 μm and the vertical angle of 90°. Herein, preferably a side length is set in the range from 10 μm to 100 μm. When the side length is set shorter than 10 μm, the diffraction effect is caused, giving the coloration. On the other hand, when the side length is set longer than 100 μm, the thickness becomes too large, giving an unfavorable structure.

A light condensing sheet practically used in an LED backlight of a liquid crystal display may be used in the present invention. Examples of such a sheet include a brightness enhancement film (BEF) manufactured by Sumitomo 3M Ltd. A shape of a prism sheet may be, for example, triangle-like stripes (i.e., with a triangle shape in the cross-sectional view) formed on a substrate may be used, each triangle-like stripe having a vertical angle of 90° and a pitch of 50 μm, or having a rounded vertical angle, a randomly changed pitch or other shapes.

Further, a light diffusion board/film may be used together with the light condensing sheet in order to control a radiation angle of light emitted from the organic EL element. For example, a light diffusion film manufactured by KIMOTO CO., LTD. (i.e., LIGHT-UP™) may be used.

<<Use>>

The organic EL element of the present invention may be used for a display and various types of luminescent sources.

Such a luminescent source includes, for example, a lighting system (e.g., home lighting or vehicle interior lighting), a backlight for watch and liquid crystal, an advertizing signboard, a traffic signal, a light source of optical storage medium, a light source of electrophotographic copying machine, a light source of optical communication processor, a light source of light sensor or the like. However, the present invention is not limited to the above examples. Among the above, especially the organic EL element of the present invention may be effectively used for a backlight of a liquid crystal display and a light source of lighting device.

The organic EL element of the present invention may be subjected to patterning when films are formed as needed by a metal mask method and an inkjet printing method or the like. When the element is subjected to patterning, only an electrode may be patterned, an electrode and a luminescent layer may be patterned, or all the layers of the element may be patterned. A conventionally known method may be used for preparing the element.

<<Display>>

Next, an embodiment of a display of the present invention including the organic EL element of the present invention will be described in detail. Specifically, an example of the display including the organic EL element of the present invention will be described referring to the drawings enclosed herewith.

FIG. 1 is a perspective diagram schematically exemplifying a structure of a display including the organic EL element of the present invention. This is a schematic diagram of, for example, a display such as a mobile phone which displays image information by luminescence of the organic EL element. As shown in FIG. 1, a display 1 includes a display unit A having a plurality of pixels and a control unit B conducting picture scanning of the display unit A.

The control unit B is electrically connected to the display unit A. The control unit B sends a scanning signal and an image data signal based on exterior image information. As a result, the respective pixels sequentially emit light corresponding to the image data signal per scanning line based on the scanning signal, thereby to display the image information on the display A.

Figure 2:
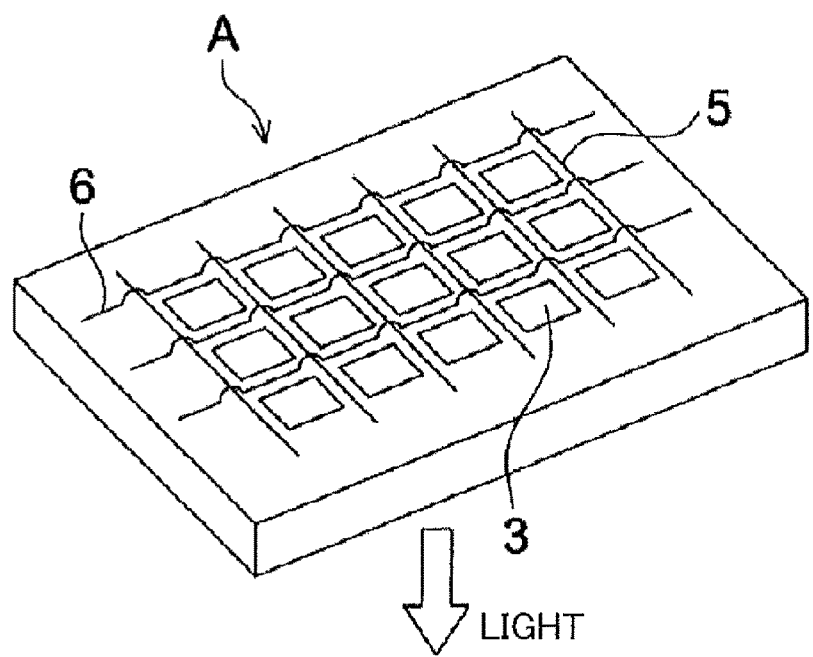
FIG. 2 is a perspective diagram schematically exemplifying a display A shown in FIG. 1

FIG. 2 is a schematic diagram of the display unit A in FIG. 1.

The display unit A includes a wiring unit having a plurality of scanning lines 5 and data lines 6, and a plurality of pixels 3.

Next, main members of the display A will be described below.

FIG. 2 shows that light emitted from the pixels 3 is extracted in a direction of the white arrow mark (i.e., downward direction). The scanning line 5 of the wiring unit and the plurality of data lines 6 are made of conductive materials, respectively. Scanning lines 5 and data lines 6 orthogonally intersect each other in a lattice shape, and are connected to respective pixels 3 at the respective orthogonal intersections (i.e., not shown in detail).

When a scanning signal is sent through a scanning line 5, a pixel 3 receives an image data signal through a data line 6, and emits light corresponding to the image data signal thus received.

When pixels with a luminescent color in a red region, pixels with a luminescent color in a green region, and pixels with luminescent color in a blue region are appropriately arranged in parallel on the same substrate, full color display may be realized.

<<Lighting Device>>

An embodiment of a lighting device having the organic EL element of the present invention will be described in detail.

Figure 3:
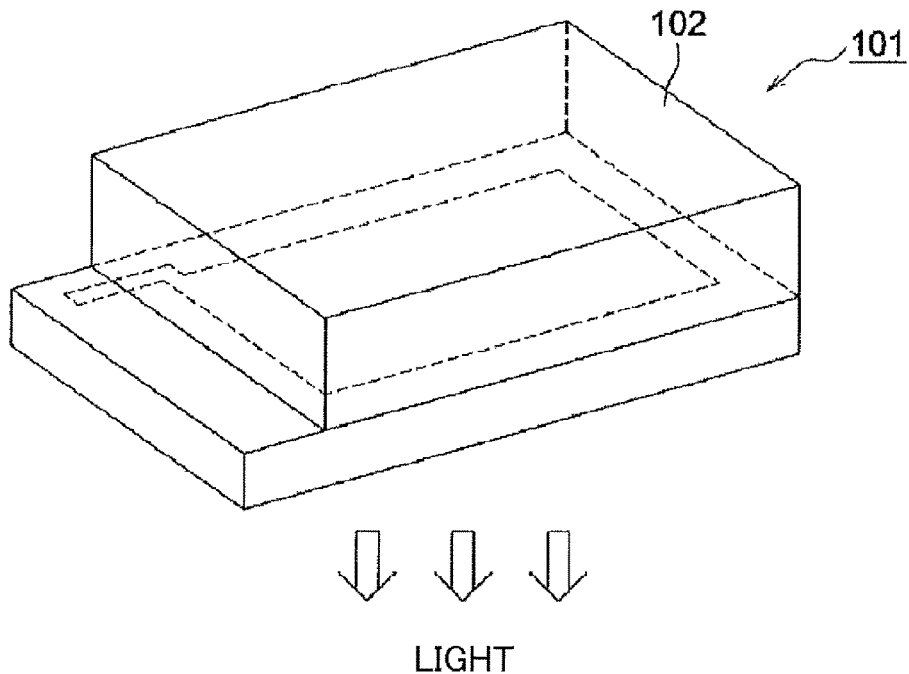
FIG. 3 is a perspective diagram schematically exemplifying a lighting device including an organic EL element of the present invention.

Lighting devices shown in FIGS. 3 and 4 are formed by using a glass substrate with a thickness of 300 μm as a sealing substrate, and an epoxy base photocurable bonding agent (TOAGOSEI CO., LTD., Luxtrack™ C0629B) as a sealing material which is applied to the circumference of the glass substrate.

For example, the lighting device is assembled by covering a non-light emitting surface of the organic EL element of the present invention with a glass cover, placing the resulting product above a cathode thereby to tightly adhere to a transparent support substrate using the photocurable bonding agent, irradiating UV light from a glass substrate side to cure the bonding agent for sealing. As a result, the lighting devices shown in FIGS. 3 and 4 may be formed.

FIG. 3 shows a schematic diagram of the lighting device. An organic EL element 101 of the present invention is covered with a glass cover 102. Note, the sealing process by the glass cover 102 is conducted under a nitrogen atmosphere (i.e., high purity nitrogen gas in 99.999% or more purity) in a glove box via preventing the organic EL element 101 from contacting to the air.

FIG. 4 is a cross-sectional view of the lighting device, indicating a cathode 105, an organic EL layer 106 and a glass substrate 107 with a transparent electrode. Herein, a nitrogen gas 108 is filled inside the glass cover 102, and a moisture catcher 109 is provided therein.

EXAMPLES

Hereinafter, the present invention will be specifically described referring to Examples. However, the present invention is not limited to those Examples. Note, in the Examples, when the terms of "part by volume" and "percentage" are described, the terms represent "volume %", unless otherwise noted. Further, the reference numbers of the host compounds and electron transfer materials used in the organic EL element of the present invention, shown in Tables 1 to 4 respectively correspond to the exemplified numbers of the compounds represented by the general formulae (A1) to (A5).

<Compounds Used in Examples>>

Comparative Compound 1

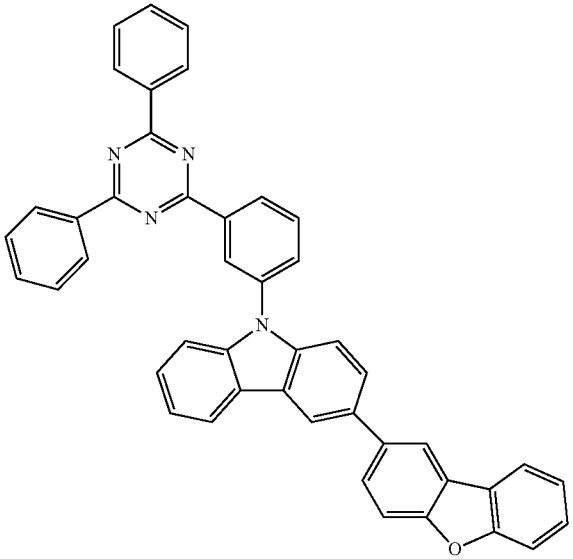

(disclosed in WO2011/019156)

Comparative Compound 2

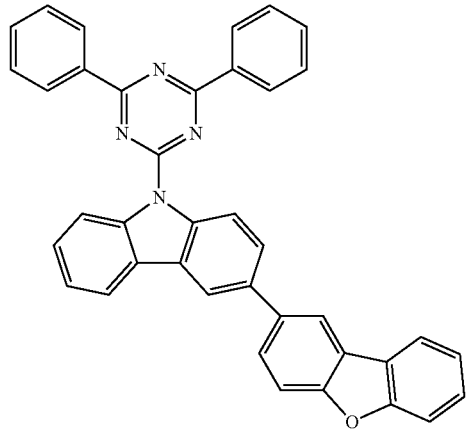

(disclosed in WO2011/019156)

Comparative Compound 3

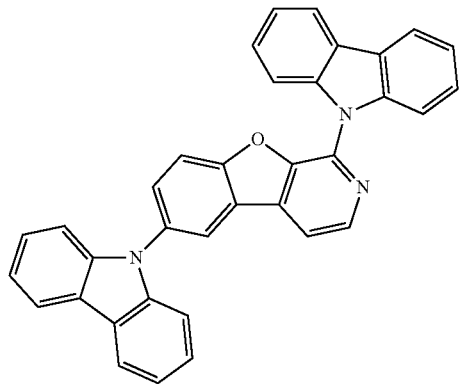

(disclosed in WO2010/083359)

-continued

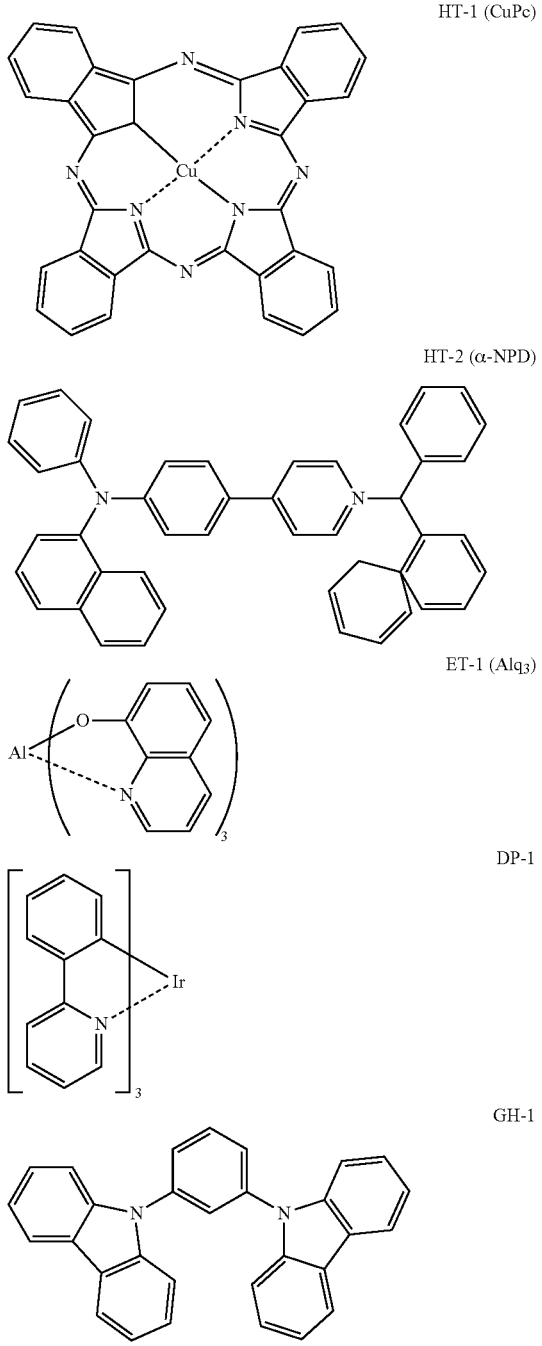

Example 1

<<Preparation of Organic EL Element 1-1>>

For preparing an anode, a substrate (NH Techno Glass, Inc., NA45) made by depositing ITO (indium tin oxide) with a thickness of 100 nm on a glass substrate (100 mm×100 mm×1.1 mm) was patterned. Then, the resulting transparent support substrate provided with the ITO transparent electrode was cleaned ultrasonically, dried under a dry nitrogen gas, and cleaned with UV ozone for 5 min.

The transparent support substrate thus prepared was fixed on a substrate holder of a commercially available vacuum vapor deposition device. HT-1 (200 mg) was put on a molybdenum resistance heating boat, HT-2 (200 mg) was put on another molybdenum resistance heating boat, DP-1 (200 mg) was put on still another molybdenum resistance heating boat, and ET-1 (200 mg) was put on still another molybdenum resistance heating boat. Then, all the molybdenum resistance heating boats were attached to the vacuum vapor deposition device.

Next, after reducing a pressure of a vacuum chamber to $4 \times 10^{-4}$ Pa, the heating boat which held HT-1 was heated by carrying a current, and HT-1 was deposited on the transparent support substrate at a deposition rate of 0.1 nm/s, thereby forming a hole injection layer with a thickness of 10 nm.

Further, the heating boat which held HT-2 was heated by carrying a current, and HT-2 was deposited on the hole injection layer at a deposition rate of 0.1 nm/s, thereby forming a hole transfer layer with a thickness of 30 nm.

Then, the heating boats which respectively held a comparative compound 1 and DP-1 were heated by carrying a current, and the comparative compound 1 and DP-1 were co-deposited on the hole transfer layer respectively at a deposition rate of 0.1 nm/s and 0.010 nm, thereby forming a luminescent layer with a thickness of 40 nm.

Next, the heating boat which held ET-1 was heated by carrying a current, and ET-1 was deposited on the luminescent layer at a deposition rate of 0.1 nm/s, thereby forming an electron transfer layer with a thickness of 30 nm.

Subsequently, lithium fluoride was deposited as an electron injection layer (i.e., a cathode buffer layer) with a thickness of 0.5 nm, and further aluminum was deposited to form a cathode, thereby preparing an organic EL element 1-1.

<<Preparation of Organic EL Elements 1-2 to 1-12>>

Organic EL elements 1-2 to 1-12 were prepared the same as the organic EL element 1-1 except that the comparative compound 1 was replaced by the host compounds listed in Table 1.

<<Evaluation of Organic EL Elements 1-1 to 1-12>>

The organic EL elements 1-1 to 1-12 thus prepared was evaluated by the following method. The method was carried out by using a glass substrate with a thickness of 300 μm as a sealing substrate, and an epoxy base photocurable bonding agent (TOAGOSEI CO., LTD., Luxtrack™ C0629B) as a sealing material which was applied to the circumference of the glass substrate.

For example, the method was carried out by covering a non-light emitting surface of each organic EL element with a glass cover, placing the resulting assembly over a cathode so that the assembly tightly adheres to the transparent support substrate via using the photocurable bonding agent, irradiating UV light from a side of the glass substrate to cure the bonding agent for sealing. As a result, the lighting devices shown in FIGS. 3 and 4 were formed and evaluated.

The respective samples thus prepared as mentioned above were evaluated as follows. Table 1 shows the evaluation results.

(1) External Extraction Quantum Efficiency (or called Luminous Efficiency)

The organic EL element was lighted up at a room temperature (from about 23° C. to about 25° C.) under a constant current condition of 2.5 mA/cm², and luminescent brightness (L) [cd/m²] was measured just after initiation of lighting. Hereby, the external extraction quantum efficiency (η) was calculated.

Here, the luminescent brightness was measured by CS-1000 (Konica Minolta Sensing, Inc.). Table 1 shows the luminescent brightness of respective samples represented by a relative value calculated by setting a value of the luminescent brightness of the organic EL element 1-1 as 100. Here, a larger value of a sample indicates that the sample is more excellent in the luminous efficiency than the comparative sample 1-1.

(2) Halflife at High Temperature

The organic EL element was driven at a constant current which made the initial brightness in 4000 cd/m² at a room temperature, and a time when light brightness therein became the half of the initial brightness was calculated. The calculated time was used as a scale of a halflife.

Next, the organic EL element was put in a thermostatic oven under a high temperature condition (about 50±5° C.), and a halflife was calculated similarly as mentioned above.

A halflife at a high temperature of each organic EL element was calculated by the following equation.

[Halflife at High Temperature (%)]=[Halflife under High Temperature Condition]/[Halflife at Room Temperature]×100

Table 1 shows the luminescent brightness of respective samples represented by a relative value calculated by setting a value of the luminescent brightness of the organic EL element 1-1 as 100. Here, a larger value of a sample indicates that the sample is more excellent in the durability against temperature changes than the comparative sample 1-1. In other words, the larger value indicates that the sample is more excellent in the luminous halflife at a high temperature than the comparative sample 1-1.

(Storage Stability at High Temperature)

The organic EL element was stored at 85° C. for 10 hr, and then stored at a room temperature for 10 hr. The above process was repeated three times. Brightness of each sample was measured before and after the storage, while driven at a constant current of 2.5 mA/cm². Then, the respective brightness rates were calculated by the following equation. The resulting brightness rates were used as a scale of storage stability at a high temperature.

[Storage Stability at High Temperature (%)]=[Brightness after Storage (2.5 mA/cm²)]/[Brightness before Storage (2.5 mA/cm²)]×100

Here, a larger value of a sample indicates that an aging variation of the luminescent intensity is smaller after the storage at a high temperature. In other words, the sample is more excellent in the storage stability at a high temperature.

Table 1 shows the evaluation results. Note, the external extraction quantum efficiency and the halflife at high temperature of respective samples are represented by relative values calculated by setting values of the organic EL element 1-1 as 100.

TABLE 1

| Organic EL Element No. | Host Compound | External Extraction Quantum Efficiency (Relative Value) | Halflife at High Temperature (Relative Value) | Storage Stability at High Temperature (%) | Note |
|---|---|---|---|---|---|
| 1-1 | Comparative Compound 1 | 100 | 100 | 63 | Comparative Example |
| 1-2 | Comparative Compound 2 | 101 | 98 | 60 | Comparative Example |
| 1-3 | (1) | 140 | 135 | 95 | Example |
| 1-4 | (2) | 130 | 128 | 92 | Example |
| 1-5 | (3) | 128 | 131 | 88 | Example |
| 1-6 | (4) | 130 | 134 | 90 | Example |
| 1-7 | (5) | 132 | 129 | 85 | Example |
| 1-8 | (6) | 129 | 130 | 83 | Example |
| 1-9 | (7) | 135 | 140 | 93 | Example |
| 1-10 | (8) | 134 | 138 | 90 | Example |
| 1-11 | (9) | 129. | 135 | 87 | Example |
| 1-12 | (10) | 125 | 120 | 80 | Example |

As clearly shown in Table 1, it is revealed that the organic EL elements 1-3 to 1-12 including the compounds of the present invention as host compounds are more excellent in the external extraction quantum efficiency, the halflife at high temperature and the storage stability at a high temperature than the comparative organic EL elements 1-1 and 1-2.

Example 2

<<Preparation of Organic EL Elements 2-1 to 2-5>>

Organic EL elements 2-1 to 2-5 were prepared the same as the organic EL element 1-1 in EXAMPLE 1 except that the comparative compound 1 was replaced with the host compounds listed in Table 2.

<<Evaluation of Organic EL Elements 2-1 to 2-5>>

The organic EL elements thus prepared were evaluated by sealing those elements similarly to the organic EL elements 1-1 to 1-12 in EXAMPLE 1, and preparing lighting devices having similar structures in FIGS. 3 and 4. Then, those lighting devices were evaluated on the same items as in EXAMPLE 1.

Table 2 shows the evaluation results. Note, the external extraction quantum efficiency and the halflife at a high temperature of respective samples are represented by relative values calculated by setting values of the organic EL element 2-1 as 100.

TABLE 2

| Organic EL Element No. | Host Compound | External Extraction Quantum Efficiency (Relative Value) | Halflife at High Temperature (Relative Value) | Storage Stability at High Temperature (%) | Note |
|---|---|---|---|---|---|
| 2-1 | Comparative Compound 3 | 100 | 100 | 65 | Comparative Example |

TABLE 2-continued

| Organic EL Element No. | Host Compound | External Extraction Quantum Efficiency (Relative Value) | Halflife at High Temperature (Relative Value) | Storage Stability at High Temperature (%) | Note |
|---|---|---|---|---|---|
| 2-2 | (11) | 128 | 135 | 90 | Example |
| 2-3 | (12) | 120 | 137 | 80 | Example |
| 2-4 | (13) | 124 | 130 | 84 | Example |
| 2-5 | (14) | 116 | 126 | 86 | Example |

As clearly shown in Table 2, it is revealed that the organic EL elements 2-2 to 2-5 including the compounds of the present invention as host compounds are more excellent in the external extraction quantum efficiency, the halflife at a high temperature and the storage stability at a high temperature than the comparative organic EL elements 2-1.

Example 3

<<Preparation of Organic EL Elements 3-1 to 3-12>>

Organic EL elements 3-1 to 3-12 were prepared the same as the organic EL element 1-1 in EXAMPLE 1 except that the comparative compound 1 used in the luminescent layer was replaced with GH-a, and ET-1 was replaced with the electron transfer materials listed in Table 3.

<<Evaluation of Organic EL Elements 3-1 to 3-12>

The organic EL elements thus prepared were evaluated by sealing those elements similarly to the organic EL elements 1-1 to 1-12 in EXAMPLE 1, and preparing lighting devices having similar structures in FIGS. 3 and 4. Then, those lighting devices were evaluated on the following items.

The following items: (1) External extraction quantum efficiency, (2) Half life at a high temperature and (3) Storage stability at a high temperature were evaluated similarly to EXAMPLE 1.

(4) Drive Voltage

Voltages when the organic EL elements were driven at a room temperature (from about 23° C. to about 25° C.) and under a constant current condition of 2.5 mA/cm2 were measured respectively, and measurement results were calculated by the following equation described below. Table 3 shows the drive voltages of the samples each represented by a relative value when a value of the organic EL element 3-1 was set as 100.

[Voltage]=[Drive Voltage of Each Organic EL Element]/[Drive Voltage of Organic EL Element 3-1]×100

Here, a smaller value of a sample indicates that the sample has a lower drive voltage than the comparative sample 3-1.

(5) Voltage Rise at Driving

Voltages of the respective organic EL elements were measured, when driven at a room temperature (from about 23° C. to 25° C.) under a constant voltage condition of 2.5 mA/cm$^2$, and measurement results were calculated by the following equation described below. Table 3 shows relative values of the respective samples to a value of the organic EL element 3-1 set as 100.

[Voltage Rise at Driving (Relative Value)]=[Drive Voltage at Halved Brightness Time]−[Initial Drive Voltage]

Here, a smaller value of a sample indicates that the sample has a smaller voltage rise at driving than the comparative sample 3-1.

Table 3 shows results in evaluation. Note, external extraction quantum efficiency, a halflife at a high temperature, a drive voltage and a voltage rise at driving are represented by relative values calculated via setting a value of the organic EL element 3-1 as 100.

TABLE 3

| Organic EL Element No. | Electron Transfer Material | External Extraction Quantum (Relative Value) | Halflife at High Temperature Relative Value | Storage Stability at High Temperature (%) | Drive Voltage | Voltage Rise At Driving | Note |
|---|---|---|---|---|---|---|---|
| 3-1 | Comparative Compound 1 | 100 | 100 | 58 | 100 | 100 | Comparative Example |
| 3-2 | Comparative Compound 1 | 103 | 104 | 55 | 96 | 104 | Comparative Example |
| 3-3 | (1) | 134 | 136 | 82 | 71 | 61 | Example |
| 3-4 | (2) | 130 | 128 | 76 | 75 | 62 | Example |
| 3-5 | (3) | 127 | 130 | 74 | 74 | 64 | Example |
| 3-6 | (4) | 130 | 135 | 86 | 60 | 50 | Example |
| 3-7 | (5) | 128 | 130 | 78 | 65 | 52 | Example |
| 3-8 | (6) | 132 | 128 | 80 | 62 | 55 | Example |
| 3-9 | (7) | 127 | 129 | 83 | 66 | 59 | Example |
| 3-10 | (8) | 128 | 125 | 75 | 70 | 62 | Example |
| 3-11 | (9) | 125 | 123 | 78 | 69 | 65 | Example |
| 3-12 | (10) | 120 | 116 | 73 | 75 | 54 | Example |

As clearly shown in Table 3, it is revealed that the organic EL elements 3-3 to 3-12 using the compounds of the present invention as electron injection materials are more excellent in the external extraction quantum efficiency, the halflife at a high temperature and the storage stability at a high temperature than the comparative organic EL elements 3-1 and 3-2. Further, it is also revealed that the organic EL elements 3-3 to 3-12 are driven at lower voltages and the voltage rises at driving are suppressed.

Example 4

<<Preparation of Organic EL Elements 4-1 to 4-17>>

Organic EL elements 4-1 to 4-17 were prepared the same as the organic EL element 3-1 in EXAMPLE 3 except that the comparative compound 1 used as an electron transfer material was replaced with the electron transfer materials listed in Table 4.

<<Evaluation of Organic EL Elements 4-1 to 4-17>

The organic EL elements thus prepared were evaluated by sealing those elements similarly to the organic EL elements 3-1 to 3-12 in EXAMPLE 3, and preparing lighting devices having similar structures in FIGS. 3 and 4. Then, those lighting devices were evaluated on the same items as in EXAMPLE 3.

Table 4 shows results in evaluation. Note, external extraction quantum efficiency, a halflife at a high temperature, a drive voltage and a voltage rise at driving are represented by relative values to a value of the organic EL element 4-1 set as 100.

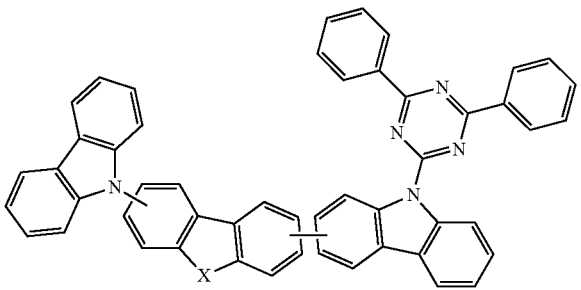

General Formula (A2)

wherein in the general formula (A2), X represents an oxygen atom or a sulfur atom;

TABLE 4

| Organic EL Element No. | Electron Transfer Material | External Extraction Quantum Efficiency (Relative Value) | Halflife at High Temperature (Relative Value) | Storage Stability at High Temperature (%) | Drive Voltage | Voltage Rise At Driving | Note |
| --- | --- | --- | --- | --- | --- | --- | --- |
| 4-1 | Comparative Compound 3 | 100 | 100 | 52 | 100 | 100 | Comparative Example |
| 4-2 | (11) | 126 | 121 | 80 | 70 | 55 | Example |
| 4-3 | (12) | 124 | 117 | 76 | 75 | 67 | Example |
| 4-4 | (13) | 120 | 113 | 70 | 73 | 62 | Example |
| 4-5 | (14) | 118 | 110 | 72 | 80 | 71 | Example |
| 4-6 | (A5-1) | 124 | 121 | 79 | 70 | 55 | Example |
| 4-7 | (A5-2) | 125 | 120 | 78 | 68 | 58 | Example |
| 4-8 | (A5-10) | 120 | 122 | 77 | 67 | 60 | Example |
| 4-9 | (A5-12) | 125 | 125 | 78 | 69 | 61 | Example |
| 4-10 | (A5-14) | 126 | 127 | 80 | 70 | 55 | Example |
| 4-11 | (A5-17) | 125 | 129 | 81 | 66 | 60 | Example |
| 4-12 | (A5-23) | 120 | 123 | 82 | 69 | 59 | Example |
| 4-13 | (A5-24) | 123 | 120 | 75 | 70 | 61 | Example |
| 4-14 | (A5-27) | 120 | 121 | 77 | 65 | 55 | Example |
| 4-15 | (A5-29) | 124 | 126 | 76 | 70 | 58 | Example |
| 4-16 | (A5-31) | 120 | 123 | 74 | 68 | 61 | Example |
| 4-17 | (A5-23) | 125 | 120 | 78 | 68 | 55 | Example |

As clearly shown in Table 4, it is revealed that the organic EL elements 4-2 to 4-17 using the compounds of the present invention as electron transfer materials are more excellent in the external extraction quantum efficiency, the halflife at a high temperature and the storage stability at a high temperature than the comparative organic EL element 4-1. Further, it is also revealed that the organic EL elements 4-2 to 4-17 are driven at lower voltages, and the voltage rises at driving are suppressed.

What is claimed is:

1. An organic electroluminescent element including an organic layer provided between at least a pair of a cathode and an anode, wherein
the organic layer is formed of at least one layer including a luminescent layer, and
at least one layer forming the organic layer contains at least one selected from compounds represented by general formulae (A2) and (A5):

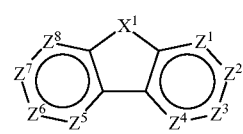

General Formula (A5)

wherein in the general formula (A5), $X^1$ represents an oxygen atom or a sulfur atom; $Z^2$, $Z^3$, $Z^5$ to $Z^8$ independently represent =N— or =C($R^1$)— respectively; $R^1$ represents a hydrogen atom or a substituent; $Z^4$ is =N—, $Z^1$ represents =N— or =C($R^2$)—, and $R^2$ represents a nitrogen-containing 6 membered heterocycle of general formula (A5-5) or (A5-6) or a nitrogen-containing 5 membered ring of general formula (A5-2);

General Formula (A5-2)

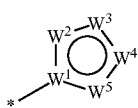

in the formula (A5-2), W$^1$ represents —N— or =C—; W$^2$ to W$^5$ independently represent =N— or =C(R$^4$)— respectively; R$^4$ represents a hydrogen atom or a substituent; at least one of W$^1$ to W$^5$ represents =N—; * represents a linkage position to the general formula (A5), and if two of =C(R$^4$)— are adjacently placed in series, two of R$^4$ may be condensed together to form a ring;

General Formula (A5-5)

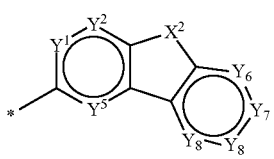

in the general formula (A5-5), Y$^1$, Y$^2$, and Y$^5$ to Y$^9$ independently represent =N— or =C(R$^3$)— respectively; R$^3$ represents a hydrogen atom or a substituent; at least one of Y$^1$, Y$^2$ and Y$^5$ represents =N—; * represents a linkage position to the general formula (A5), X$^2$ represents one member selected from an oxygen atom, a sulfur atom, —NR$^2$—, and —CR$^3$R$^4$—, wherein R$^2$ and R$^4$ are identical to said R$^2$ and R$^4$, respectively;

General Formula (A5-6)

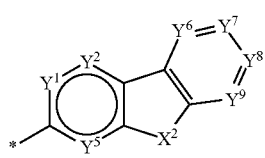

in the general formula (A5-6), Y$^1$, Y$^2$ and Y$^5$ to Y$^9$ independently represent =N— or =C(R$^3$)— respectively; R$^3$ represents a hydrogen atom or a substituent; at least one of Y$^1$, Y$^2$ and Y$^5$ represents =N—; * represents a linkage position to the general formula (A5), X$^2$ represents one member selected from an oxygen atom, a sulfur atom, —NR$^2$— or —CR$^3$R$^4$—, wherein R$^2$ and R$^4$ are identical to said R$^2$ and R$^4$, respectively.

2. An organic electroluminescent element including an organic layer provided between at least a pair of a cathode and an anode, wherein
the organic layer is formed of at least one layer including a luminescent layer, and
at least one layer forming the organic layer contains at least one selected from compounds represented by general formulae (A2) and (A5):

General Formula (A2)

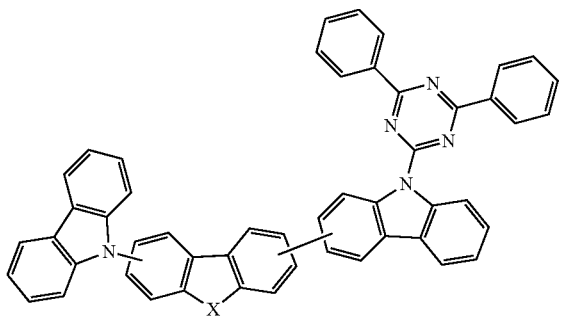

wherein in the general formula (A2), X represents an oxygen atom or a sulfur atom;

General Formula (A5)

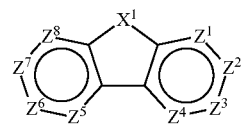

wherein in the general formula (A5), X$^1$ represents an oxygen atom or a sulfur atom; Z$^2$, Z$^3$, Z$^5$ to Z$^8$ independently represent =N— or =C(R$^1$)— respectively; R$^1$ represents a hydrogen atom or a substituent; Z$^4$ is =N—, Z$^1$ represents =N— or =C(R$^2$)—, and R$^2$ represents a nitrogen-containing 6 membered heterocycle of general formula (A5-7) or (A5-8) or a nitrogen-containing 5 membered ring of general formula (A5-2);

General Formula (A5-2)

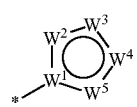

in the formula (A5-2), W$^1$ represents —N— or =C—; W$^2$ to W$^5$ independently represent =N— or =C(R$^4$)— respectively; R$^4$ represents a hydrogen atom or a substituent; at least one of W$^1$ to W$^5$ represents =N—; * represents a linkage position to the general formula (A5), and if two of =C(R$^4$)— are adjacently placed in series, two of R$^4$ may be condensed together to form a ring;

General Formula (A5-7)

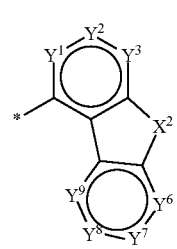

wherein in the general formula (A5-7), $Y^1$ to $Y^3$, and $Y^6$ to $Y^9$ independently represent =N— or =C($R^3$)— respectively; $R^3$ represents a hydrogen atom or a substituent; at least one of $Y^1$ to $Y^3$ represents =N—; * represents a linkage position to the general formula (A5), $X^2$ represents one member selected from an oxygen atom, a sulfur atom, —$NR^2$— or —$CR^3R^4$, $R^2$ and $R^4$ are identical to said $R^2$ and $R^4$, respectively;

General Formula (A5-8)

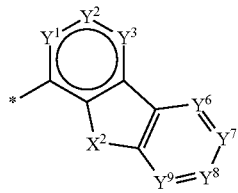

wherein in the general formula (A5-8), $Y^1$ to $Y^3$, and $Y^6$ to $Y^9$ independently represent =N— or =C($R^3$)— respectively; $R^3$ represents a hydrogen atom or a substituent; at least one of $Y^1$ to $Y^3$ represents =N—; * represents a linkage position to the general formula (A5), $X^2$ represents one member selected from an oxygen atom, a sulfur atom, —$NR^2$— or —$CR^3R^4$—, $R^2$ and $R^4$ are identical to said $R^2$ and $R^4$, respectively.

3. An organic electroluminescent element including an organic layer provided between at least a pair of a cathode and an anode, wherein the organic layer is formed of at least one layer including a luminescent layer, and at least one layer forming the organic layer contains at least one selected from compounds (4) to (6) and (11) to (14):

(4)

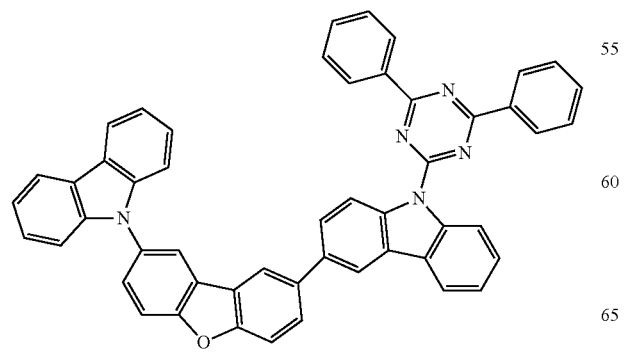

(5)

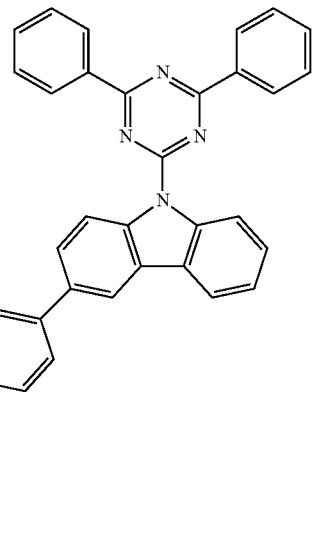

(6)

(11)

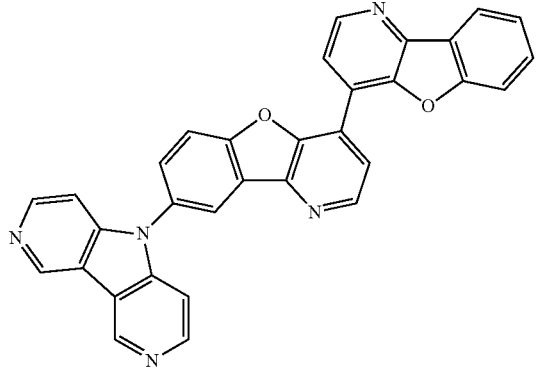

(12)

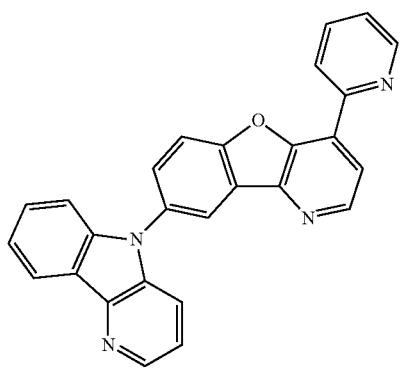

General Formula (A1)

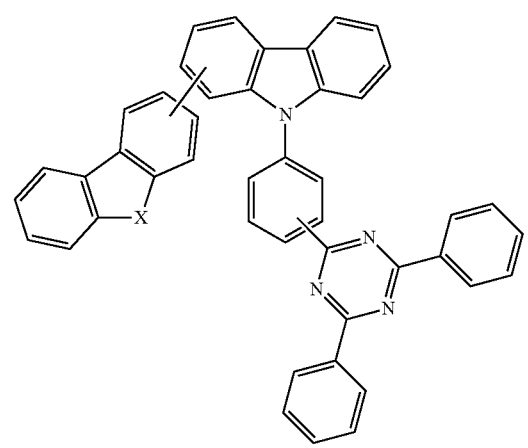

(13)

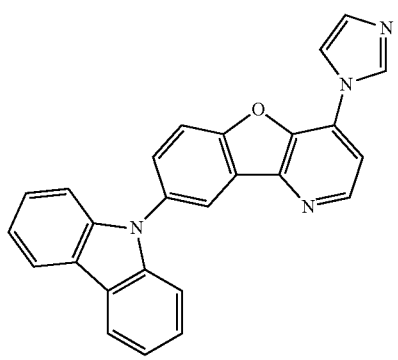

General Formula (A2)

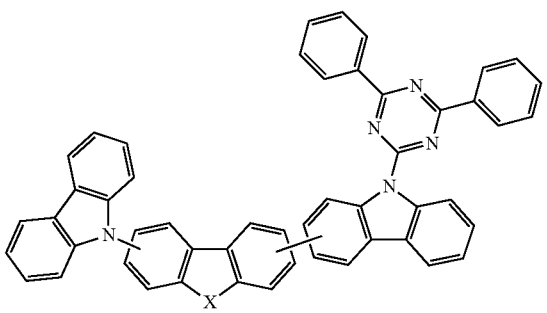

(14)

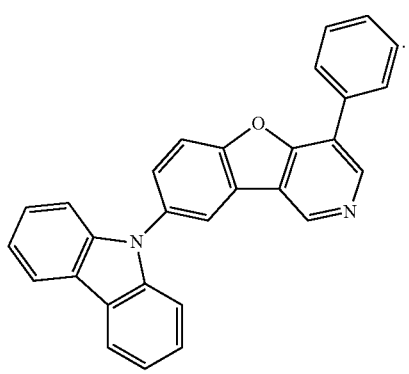

General Formula (A3)

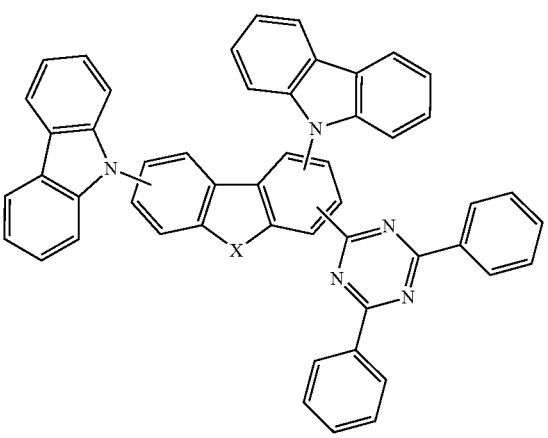

4. An organic electroluminescent element including an organic layer provided between at least a pair of a cathode and an anode, wherein the organic layer is formed of at least one layer including a luminescent layer, and at least one layer forming the organic layer contains at least one selected from compounds represented by general formulae (A1) to (A5):

wherein in the general formulae (A1) to (A3), X represents an oxygen atom or a sulfur atom;

General Formula (A4)

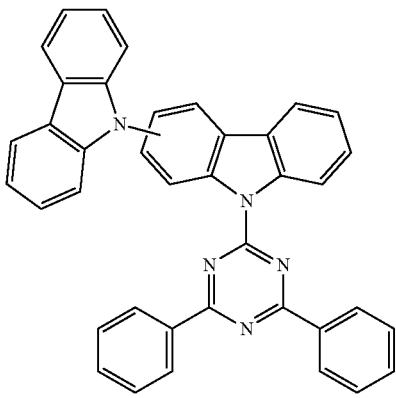

General Formula (A5)

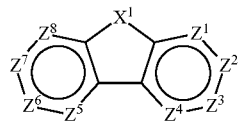

wherein in the general formula (A5), $X^1$ represents an oxygen atom or a sulfur atom; $Z^1$ to $Z^8$ independently represent =N— or =C($R^1$)— respectively; $R^1$ represents a hydrogen atom or a substituent; at least one of $Z^1$ to $Z^4$ represents =N—, if $Z^4$ is =N—, $Z^1$ represents =N— or =C($R^2$)—, and $R^2$ represents a nitrogen-containing 6 membered heterocycle of general formula (A5-1) or a nitrogen-containing 5 membered ring of general formula (A5-2), if $Z^4$ is =C($R^1$)—, at least $Z^3$ represents =N—;

General Formula (A5-1)

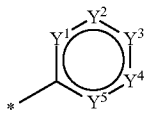

wherein in the formula (A5-1), $Y^1$ to $Y^5$ independently represent =N— or =C($R^3$)— respectively; $R^3$ represents a hydrogen atom or a substituent; at least one of $Y^1$ to $Y^5$ represents =N—; * represents a linkage position to the general formula (A5), if two of =C($R^3$)— are adjacently placed in series, two of $R^3$ may be condensed together to form a ring;

General Formula (A5-2)

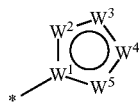

wherein in the formula (A5-2), $W^1$ represents —N— or =C—; $W^2$ to $W^5$ independently represent =N— or =C($R^4$)— respectively; $R^4$ represents a hydrogen atom or a substituent; at least one of $W^1$ to $W^5$ represents =N—; * represents a linkage position to the general formula (A5), if two of =C($R^4$)— are adjacently placed in series, two of $R^4$ may be condensed together to form a ring;

wherein the luminescent layer includes an electron transfer layer, and the electron transfer layer contains at least one of the compounds represented by the general formulae (A1) to (A5).

5. A method for producing an organic electroluminescent element, wherein the organic electroluminescent element described in claim 1 is prepared by a wet process.

6. A display comprising the organic electroluminescent element described in claim 1.

7. A lighting device comprising the organic electroluminescent element described in claim 1.

* * * * *